(12) United States Patent
Chen et al.

(10) Patent No.: US 11,643,678 B2
(45) Date of Patent: May 9, 2023

(54) METHOD FOR ANALYSIS OF YEAST

(71) Applicant: SHANGHAI RUIYU BIOTECH CO., LTD., Shanghai (CN)

(72) Inventors: Rui Chen, Shanghai (CN); Haohan Xia, Shanghai (CN)

(73) Assignee: SHANGHAI RUIYU BIOTECH CO., LTD., Shanghai (CN)

( * ) Notice: Subject to any disclaimer, the term of this patent is extended or adjusted under 35 U.S.C. 154(b) by 0 days.

(21) Appl. No.: 17/806,479

(22) Filed: Jun. 11, 2022

(65) Prior Publication Data

US 2022/0372539 A1 Nov. 24, 2022

Related U.S. Application Data

(63) Continuation of application No. PCT/CN2020/134466, filed on Dec. 8, 2020.

(30) Foreign Application Priority Data

Dec. 11, 2019 (CN) .......................... 201911264590.8

(51) Int. Cl.
 *C12Q 1/06* (2006.01)
 *G06T 7/62* (2017.01)
 *G06T 7/00* (2017.01)

(52) U.S. Cl.
 CPC .............. *C12Q 1/06* (2013.01); *G06T 7/0002* (2013.01); *G06T 7/62* (2017.01); *G06T 2207/10056* (2013.01); *G06T 2207/30242* (2013.01)

(58) Field of Classification Search
 CPC ............ G06T 2207/10056; G06T 2207/30128
 See application file for complete search history.

(56) References Cited

U.S. PATENT DOCUMENTS

| | | | |
|---|---|---|---|
| 2015/0142732 A1* | 5/2015 | Pace .................... | G06F 16/5838 707/722 |
| 2018/0196037 A1 | 7/2018 | Polwart et al. | |
| 2019/0258046 A1 | 8/2019 | Gallagher-Gruber | |
| 2021/0285864 A1* | 9/2021 | Ozcan ................... | G06T 7/0004 |
| 2022/0317049 A1* | 10/2022 | Chen ......................... | G06T 7/62 |
| 2022/0372539 A1* | 11/2022 | Chen .................... | G06T 7/0002 |

FOREIGN PATENT DOCUMENTS

| | | | |
|---|---|---|---|
| CN | 1825158 A | | 8/2006 |
| CN | 101607263 A | | 8/2010 |
| CN | 101982780 A | | 3/2011 |
| CN | 104406519 A | * | 3/2015 |

(Continued)

OTHER PUBLICATIONS

First Office Action in Chinese Application No. 201911264590.8 dated Mar. 8, 2021, 21 pages.

(Continued)

*Primary Examiner* — Gandhi Thirugnanam
(74) *Attorney, Agent, or Firm* — Metis IP LLC

(57) ABSTRACT

A method for analysis of yeast includes: receiving a microscopic image of yeast by a cloud server (2901), the microscopic image including a scaling pattern for determining a magnification; determining the magnification by the cloud server based on the scaling pattern (2902); and analyzing, by the cloud server, the microscopic image based on the magnification to obtain an analysis result (2903).

20 Claims, 30 Drawing Sheets

(56) References Cited

FOREIGN PATENT DOCUMENTS

| CN | 104406519 | A | | 3/2015 | |
|---|---|---|---|---|---|
| CN | 104830680 | A | | 8/2015 | |
| CN | 104990907 | A | | 10/2015 | |
| CN | 107144520 | A | | 9/2017 | |
| CN | 108693097 | A | | 10/2018 | |
| CN | 110866918 | A | * | 3/2020 | ............... C12Q 1/06 |
| CN | 110866918 | A | | 3/2020 | |
| CN | 110991379 | B | * | 2/2022 | ......... G06K 9/00147 |
| EP | 3474310 | | | 4/2019 | |
| WO | 2014161585 | A1 | | 10/2014 | |

OTHER PUBLICATIONS

The Second Office Action in Chinese Application No. 201911264590.8 dated Jul. 9, 2021, 21 pages.
The Third Office Action in Chinese Application No. 201911264590.8 dated Oct. 21, 2021, 18 pages.
Decision to Grant a Patent in Chinese Application No. 201911264590.8 dated Jan. 20, 2022, 2 pages.
International Search Report in PCT/CN2020/134466 dated Mar. 10, 2021, 7 pages.
Written Opinion in PCT/CN2020/134466 dated Mar. 10, 2021, 8 pages.
Anonymity, JX-2000 Optical Microscope with Image Analyzer, http://cdjx.caco3.net/company/sell/itemid-728.shtml, 2018, 6 pages.
The Extended European Search Report in European Application No. 20900523.0 dated Dec. 19, 2022, 8 pages.

* cited by examiner

METHOD FOR ANALYSIS OF YEAST

CROSS-REFERENCE TO RELATED APPLICATIONS

This application is a continuation of International Application No. PCT/CN2020/134466, filed on Dec. 8, 2020, which designates the United States of America and claims priority to Chinese Patent Application No. CN201911264590.8, filed on Dec. 11, 2019, the contents of which are incorporated herein by reference in their entirety.

TECHNICAL FIELD

The present disclosure relates to a method for analysis of yeast.

BACKGROUND

From ancient times to the present, yeast have been closely related to human life. And the yeast have been widely used in food production, wine brewing, scientific research, and other fields. Based on the demand of modern industrial production and quality control, accurately counting of the yeast has become a more and more important link.

SUMMARY

One aspect of the present disclosure provides a method for analysis of yeast. The method comprises: receiving a microscopic image of yeast by a cloud server, wherein the microscopic image includes a scaling pattern for determining a magnification; determining the magnification by the cloud server based on the scaling pattern; and analyzing, by the cloud server, the microscopic image based on the magnification to obtain an analysis result.

In some embodiments of the present disclosure, the analysis result includes at least one of a concentration of alive yeast, a concentration of dead yeast, a total concentration of the yeast, a mortality rate of the yeast, a survival rate of the yeast, an average diameter of the yeast, an average circularity of the yeast, a bud rate of the yeast, or an aggregation rate.

In some embodiments of the present disclosure, the analyzing the microscopic image based on the magnification comprises:

performing, by the cloud server, an image processing operation on the microscopic image to determine a count of the alive yeast and a count of the dead yeast in the microscopic image.

In some embodiments of the present disclosure, the method further comprises:

capturing the microscopic image of the yeast in a sample cell on a sample plate by a microscopic device and transmitting the microscopic image to the cloud server;

obtaining a depth of the sample cell by the cloud server; and determining, by the cloud server, the total concentration of the yeast, the concentration of the alive yeast, the concentration of the dead yeast based on the depth of the sample cell, the count of the alive yeast, the count of the dead yeast and the magnification.

In some embodiments of the present disclosure, the cloud server determines the concentration of the alive yeast based on the count of the alive yeast and the count of the dead yeast.

In some embodiments of the present disclosure, the analyzing the microscopic image based on the magnification includes determining a diameter of each yeast and a total count of the yeast by the cloud server based on the magnification; and determining the average diameter of the yeast based on the diameter of each yeast and the total count of the yeast.

In some embodiments of the present disclosure, the cloud server performs an image processing operation on the microscopic image to determine a circularity of each yeast and the total count of the yeast, and the cloud server determines the average circularity of the yeast based on the circularity of each yeast and the total count of the yeast.

In some embodiments of the present disclosure, the cloud server performs an image processing operation on the microscopic image to determine the total count of the yeast and a count of budding yeast, and the cloud server determines the bud rate of the yeast based on the total count of the yeast and the count of the budding yeast.

In some embodiments of the present disclosure, the cloud server performs an image processing operation on the microscopic image to determine the total count of the yeast and a count of aggregated yeast, and the cloud server determines the aggregation rate based on the total count of the yeast and the count of the aggregated yeast.

In some embodiments of the present disclosure, the method for analysis of yeast further comprises:

capturing the microscopic image of the yeast in a sample cell on a sample plate by a microscopic device and transmitting the microscopic image to the cloud server.

In some embodiments of the present disclosure, the sample plate includes the scaling pattern.

In some embodiments of the present disclosure, the scaling pattern is located at the bottom of the sample cell.

In some embodiments of the present disclosure, the sample plate includes a plurality of sample cells, and the scaling pattern is arranged at the bottom of each sample cell.

In some embodiments of the present disclosure, the scaling pattern is located near the sample cell.

In some embodiments of the present disclosure, the scaling pattern includes a first tick mark extending in a first direction.

In some embodiments of the present disclosure, the scaling pattern includes a plurality of first tick marks, and the plurality of first tick mark are arranged in a second direction that is different from the first direction.

In some embodiments of the present disclosure, the first direction is perpendicular to the second direction.

In some embodiments of the present disclosure, the sample cell extends in the first direction or the second direction.

In some embodiments of the present disclosure, the scaling pattern further includes a second tick mark extending in the second direction.

In some embodiments of the present disclosure, the scaling pattern further includes a first mark for determining an extension direction and an arrangement direction of the sample cell.

In some embodiments of the present disclosure, the first mark includes a first arrow and a second arrow, which are perpendicular to each other.

In some embodiments of the present disclosure, the scaling pattern further includes a second mark for identifying the sample plate.

In some embodiments of the present disclosure, the scaling pattern further includes a third mark for identifying the sample cell.

In some embodiments of the present disclosure, obtaining the depth of the sample cell includes determining the depth of the sample cell on the sample plate based on the second mark.

In some embodiments of the present disclosure, obtaining the depth of the sample cell includes determining the depth of the sample cell on the sample plate based on the third mark.

Other features of the present disclosure and advantages thereof may become apparent from the following detailed description of embodiments of the present disclosure with reference to the drawings.

BRIEF DESCRIPTION OF THE DRAWINGS

The drawings forming a portion of the present disclosure describe embodiments of the present disclosure and are used together with the present disclosure to explain the principles of the present disclosure.

Referring to the drawings, the present disclosure may be more clearly understood according to the following detailed description, wherein.

Figure 1:
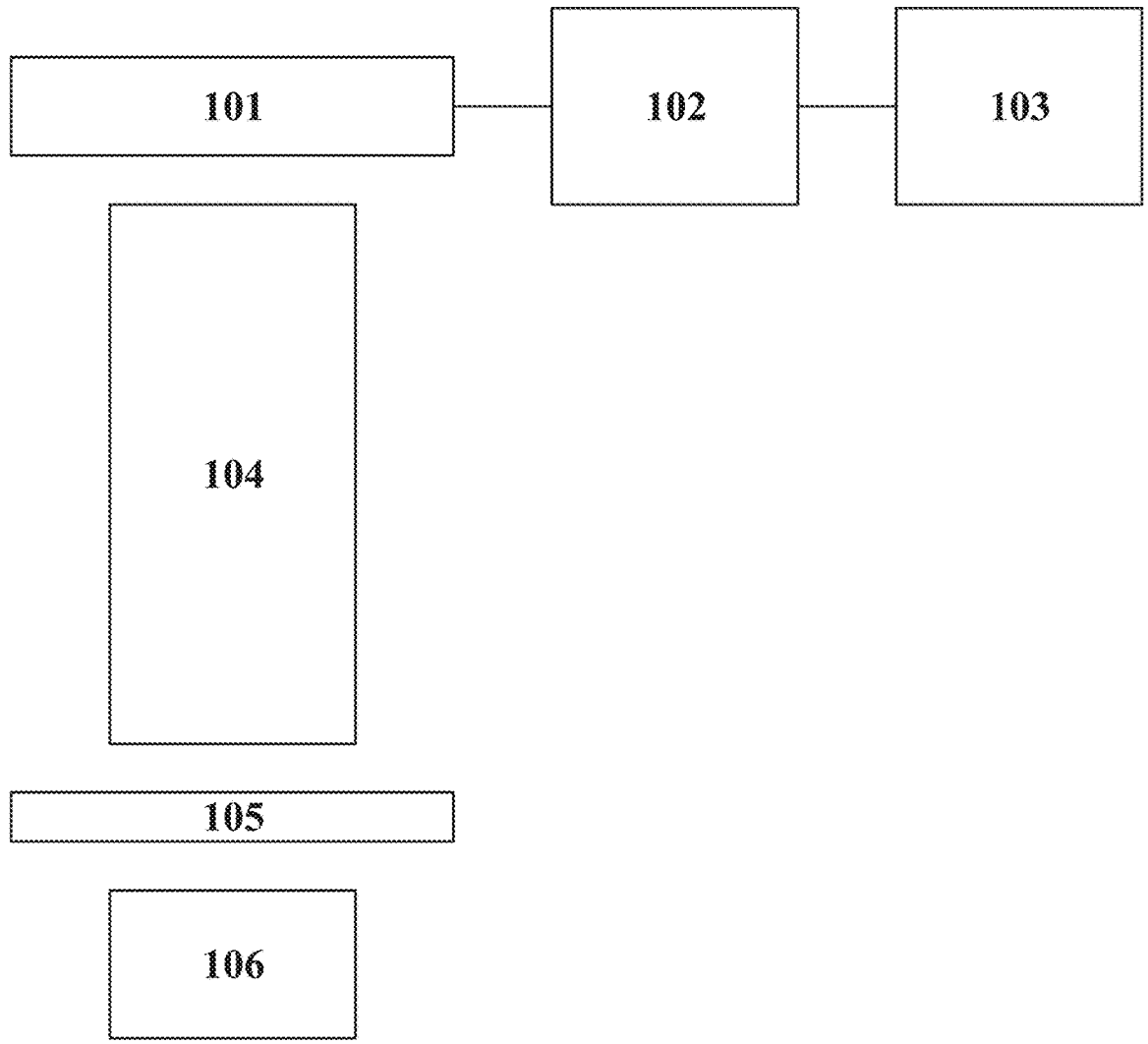
FIG. 1 is a schematic diagram illustrating a microscopic device according to some embodiments of the present disclosure.

It should be noted that in some embodiments described below, the same number is used between different drawings to indicate the same part or a part with the same function, and the repeated description thereof is omitted. In the present disclosure, similar labels and letters are used to indicate similar items. Therefore, once an item is defined in a drawing, a further discussion may not need to be described in subsequent drawings.

In order to facilitate understanding, position, size, range of each structure shown in the drawings or the like may not indicate the actual position, size, or range in some cases. Therefore, the present disclosure is not limited to the position, dimension, ranges disclosed in the drawings, or the like.

DETAILED DESCRIPTION

The embodiments of the present disclosure are described in detail with reference to the drawings. It should be noted that unless stated otherwise or obvious from the context, the relative arrangement of components and steps, numerical expressions, and values set forth in these embodiments do not limit the scope of the present disclosure.

The following description of at least one embodiment is merely illustrative in nature and is in no way intended to limit the present disclosure and its application or use.

The techniques, methods, and devices known to those of ordinary skill in the art may not be discussed in detail, but where appropriate, such techniques, methods, and devices should be considered as a part of the present disclosure.

In all the examples shown and discussed in the present disclosure, any specific value should be interpreted as merely for example, and not as a limitation. Therefore, other examples of the embodiments may have different values.

FIG. 1 is a schematic diagram illustrating a microscopic device according to some embodiments of the present disclosure.

As shown in FIG. 1, the microscopic device 100 may include an image sensor 101, a memory 102, a processor 103, an optical imaging device 104, a sample table 105, and a light source 106. During an operation, a sample plate may be arranged on the sample table 105. The light source 106 may emit light towards the sample plate. The optical imaging device 104 may include, for example, an objective and an eyepiece (not shown). Each of the objective and the eyepiece may be composed of one or more sets of lenses. An optical image generated by the optical device 104 may be received by the image sensor 101 and converted into a digital image by the image sensor 101. The image sensor may be, for example, a charge-coupled device (CCD), a complementary metal-oxide semiconductor (CMOS), or the like. In some embodiments according to the present disclosure, an image capturing device such as a mobile phone, or a camera may also be arranged in an optical path. The image capturing device may also include image sensors, and may capture an image of a sample in the sample plate through the optical device 104.

The digital image captured by the image sensor 101 may be stored in the memory 102, and the processor 103 may read and process the digital image in the memory 102.

Figure 2:
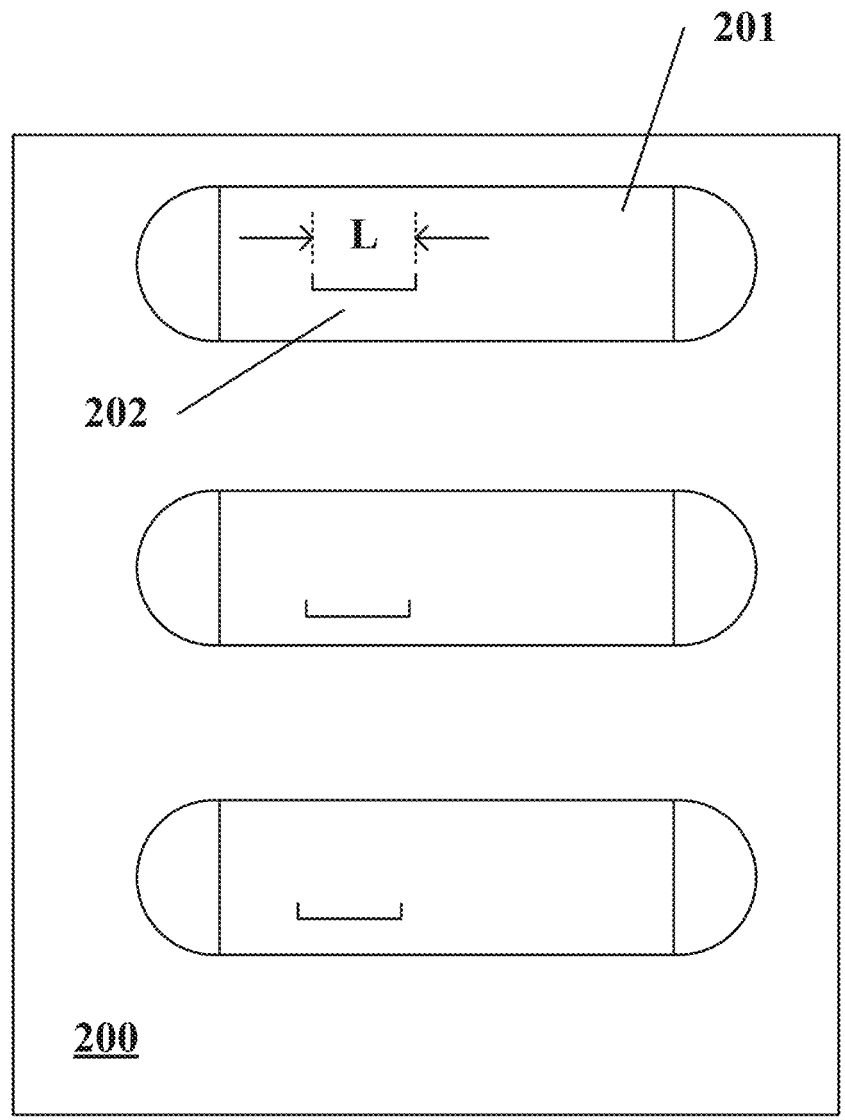
FIG. 2 is a schematic diagram illustrating a sample plate according to some embodiments of the present disclosure.

FIG. 2 is a schematic diagram illustrating a sample plate according to some embodiments of the present disclosure. As shown in FIG. 2, a sample plate 200 may include a plurality of sample cells 201 in which samples may be accommodated. In addition, the sample plate 200 may also include a scaling pattern 202.

In the embodiments shown in FIG. 2, the scaling pattern 202 is located at the bottom of a sample cell (i.e., on the surface where the sample cell contacts the sample). When capturing an image of a sample by the microscope device 100, the optical imaging device 104 may focus on the bottom of the sample cell, and set the scaling pattern 202 at the bottom of the sample cell to capture a clear image of the scaling pattern while capturing the sample image. The scaling pattern 202 may be a line segment along a horizontal direction with a length of L. For example, in some embodiments, L may be 1 μm-100 μm. Using the scaling pattern 202, the magnification of the microscopic device 100 may be accurately obtained.

Figure 13:
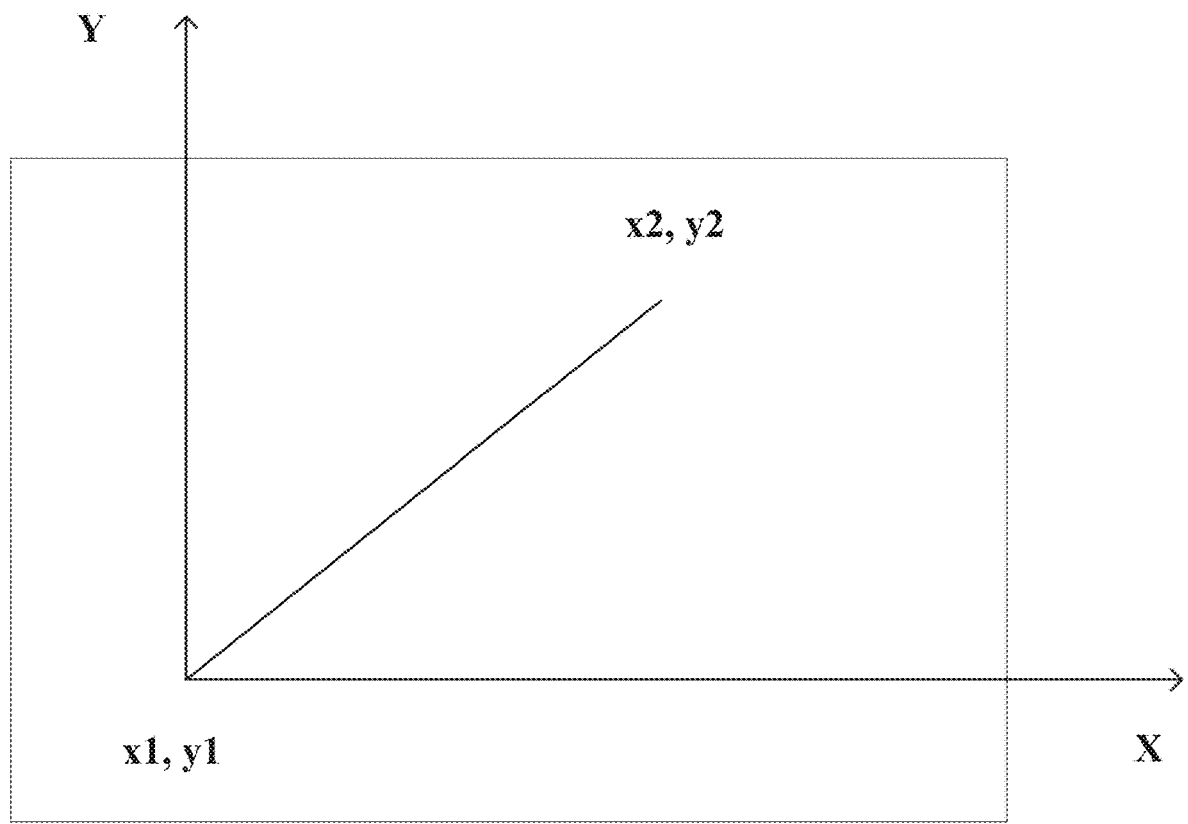
FIG. 13 is a schematic diagram illustrating an arrangement direction of pixels of an image sensor according to some embodiments of the present disclosure.

For example, as shown in FIG. 13, for the image sensor 101 whose pixels are evenly arranged in two directions perpendicular to each other (the X direction and the Y direction), if coordinates at both ends of the line segment of the scaling pattern 202 are (x1, y1) and (x2, y2) in the digital image generated by the image sensor 101, respectively. Then, the coordinates (x1, y1) and (x2, y2) represent positions of the pixels corresponding to both ends of the line segment on the image sensor 101. Then, a size k of an image of the line segment generated by the line segment on the sample plate on the image sensor 101 may be determined based on a formula (1):

$$K = D \cdot \text{sqrt}[(x2-x1)^2 + (y2-y1)^2] \quad (1)$$

where D represents spacing between adjacent pixels in the image sensor 101, that is, a distance from a center of a pixel to a center of an adjacent pixel of the pixel along the X direction or Y direction. The function "sqrt" represents determining a square root.

Then, a magnification M of the optical imaging device 104 of the microscope device 100 may be determined based on the following formula (2):

$$M = K/L \quad (2)$$

In the above method, an actual magnification of the microscopic device 100 may be accurately obtained.

In the above embodiment, a pixel array of the image sensor 101 may be a rectangular array, and the spacing of the adjacent pixels may be the same in the X direction and the Y direction. In other embodiments according to the present disclosure, the spacing between the adjacent pixels of the image sensor 101 may be different in the X direction and the Y direction. For example, if the spacing between the adjacent pixels along the X direction is D1 and the spacing between adjacent pixels along the Y direction is D2, the size k of the image of the line segment generated by the line segment on the sample plate on the image sensor 101 may be determined based on the following formula (3):

$$K = \text{sqrt}[(D1)^2 \cdot (x2-x1)^2 + (D2)^2 \cdot (y2-y1)^2] \quad (3)$$

Then, the actual magnification M of the microscopic device 100 may be accurately obtained.

The above operation of determining the actual magnification may be performed by, for example, the processor 103 of the microscope device 100. For example, the spacing between adjacent pixels of the image sensor 101 may be stored in the memory 102 in advance. When the image sensor 101 generates a digital image of the sample plate 200, the digital image may be stored in the memory 102.

Then, the processor 103 may read the digital image from the memory 102 and recognize the scaling pattern in the digital image. Next, the processor 103 may read the spacing between adjacent pixels of the image sensor 101 from the memory and determine the actual magnification M of the microscopic device 101 based on the above formulas (1)-(3).

In addition, in some embodiments according to the present disclosure, for the sample plate 200 with a plurality of sample cells 201, the magnification M may also be determined using the following method.

For the sample plate 200 shown in FIG. 2 with three sample cells 201, the corresponding magnifications M1, M2, and M3 may be determined respectively based on the scaling pattern 202 on each of the sample cells 201, and then the actual magnification M of the microscopic device may be calculated by a formula (4):

$$M = (M1 + M2 + M3)/3 \quad (4)$$

That is, an average value of the magnifications M1, M2, and M3 are designated as the actual magnification M of the microscopic device. In this way, the calculation error may be reduced and the accuracy of magnification may be further improved.

In addition, in other embodiments according to the present disclosure, a sum K' of the line segments of each scaling pattern 202 may be determined based on the following formula (5):

$$K'=D\cdot\text{sqrt}[(x2-x1)^2+(y2-y1)^2]+D\text{ sqrt}[(x3-x4)^2+(y3-y4)^2]+D\text{ sqrt}[(x5-x6)^2+(y5-y6)^2] \quad (5)$$

where (x1, y1) and (x2, y2) are the coordinates of both ends of the line segment of the scaling pattern of a first sample cell 201 in the upper of FIG. 2 in the digital image; (x3, y3) and (x4, y4) are the coordinates of both ends of the line segment of the scaling pattern of a second sample cell 201 in the upper of FIG. 2 in the digital image, (x5, y5) and (x6, y6) are the coordinates of both ends of the line segment of the scaling pattern of a third sample cell 201 in the lower of FIG. 2 in the digital image.

Then, the actual magnification M of the microscopic device may be determined based on a formula (6):

$$M=K'/(3L) \quad (6)$$

In this way, the calculation error may be reduced and the accuracy of magnification may be further improved.

The above embodiments briefly describe how to determine the actual magnification of the microscopic device 100 based on the scaling pattern on the sample plate. It should be understood that the present disclosure is not limited to the above methods. Under the instruction and enlightenment of the present disclosure, those skilled in the art may also adopt other ways to determine the actual magnification of the microscopic device 100 based on the scaling pattern.

Figure 3:
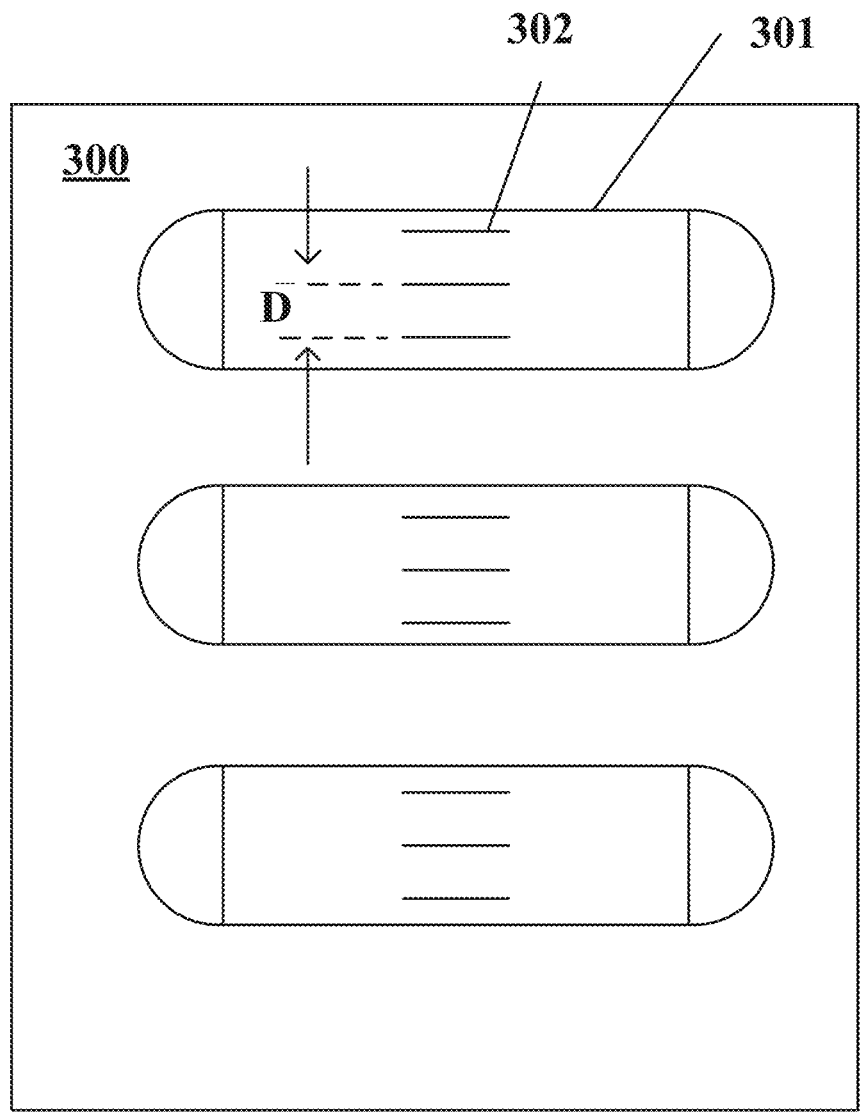
FIG. 3 is another schematic diagram illustrating a sample plate according to some embodiments of the present disclosure.

FIG. 3 is another schematic diagram illustrating an sample plate according to some embodiments of the present disclosure. As shown in FIG. 3, a sample plate 300 may include a plurality of sample cells 301 in which samples to be observed and captured may be accommodated. In addition, the sample plate 300 also has a scaling pattern 302.

In the embodiments shown in FIG. 3, the scaling pattern 302 may be located at the bottom of the sample cell. The scaling pattern 302 may be tick marks arranged at an equal interval, each tick mark may extend along the horizontal direction (a first direction), and spacing of the tick marks in the vertical direction (a second direction) is D. In some embodiments according to the present disclosure, the spacing D may be, for example, 1 μm-10 μm. The magnification of the microscopic device may be accurately determined based on the scaling pattern 302.

For example, based on the digital image generated by the image sensor 101, the processor 103 may obtain a coordinate (x1', y1') of a point on a tick mark in the scaling pattern 302 and a coordinate (x2', y2') of an intersection point of a line along the direction vertical to the tick mark and passing through point (x1', y1') and an adjacent tick mark.

Using a method similar to the method described above, the actual magnification of the microscopic device 100 may be determined.

In the example shown in FIG. 3, a plurality of tick marks 302 may be arranged on each sample cell. When the magnification of the microscopic device 100 is relatively large, the actual magnification may be accurately determined even if only a portion of a sample cell is included in the visual field.

Figure 4:
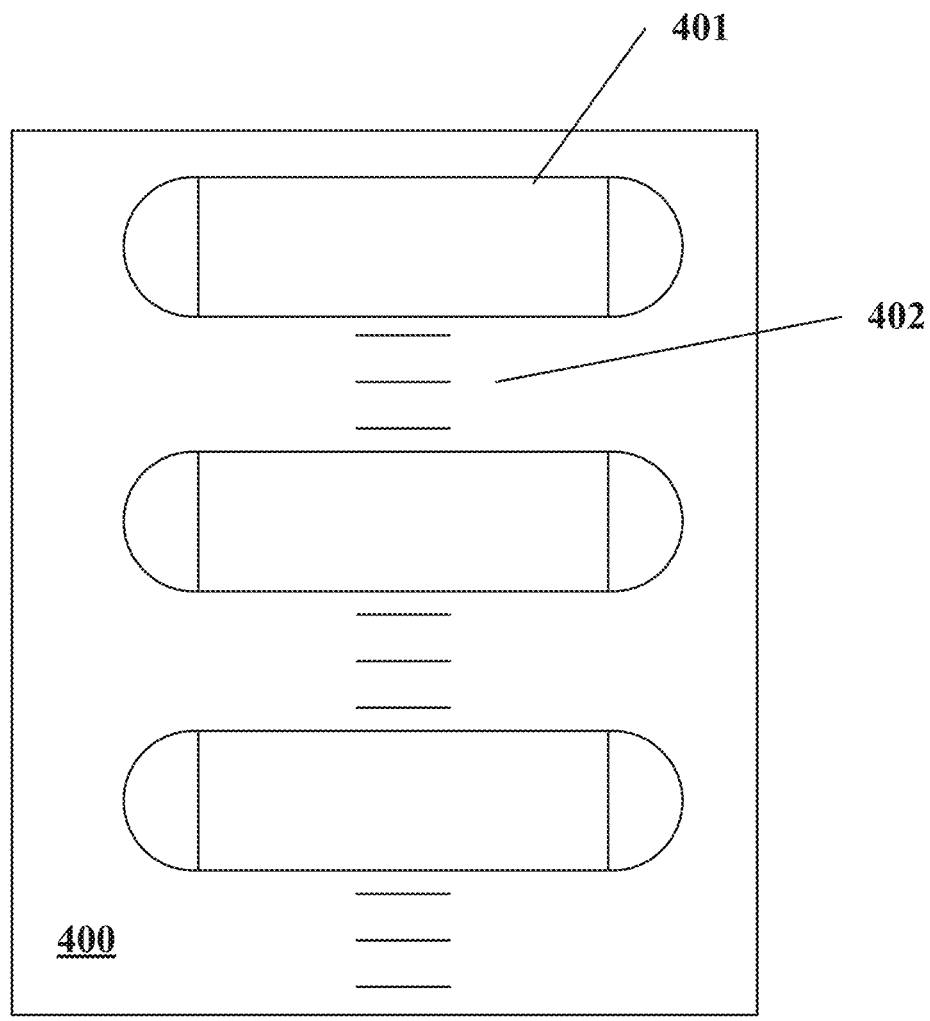
FIG. 4 is another schematic diagram illustrating a sample plate according to some embodiments of the present disclosure.

FIG. 4 is another schematic diagram illustrating a sample plate 400 according to some embodiments of the present disclosure. As shown in FIG. 4, in the sample plate 400, the scaling pattern 402 may be arranged outside a sample cell 401. In this way, interference of the scaling pattern 402 on the sample in the sample cell 401 may be avoided, and a sample may be more clearly observed and analyzed. In order to capture a clear image of the scaling pattern 402, the scaling pattern 402 may be located on the same plane as the bottom of the sample cell.

Figure 5:
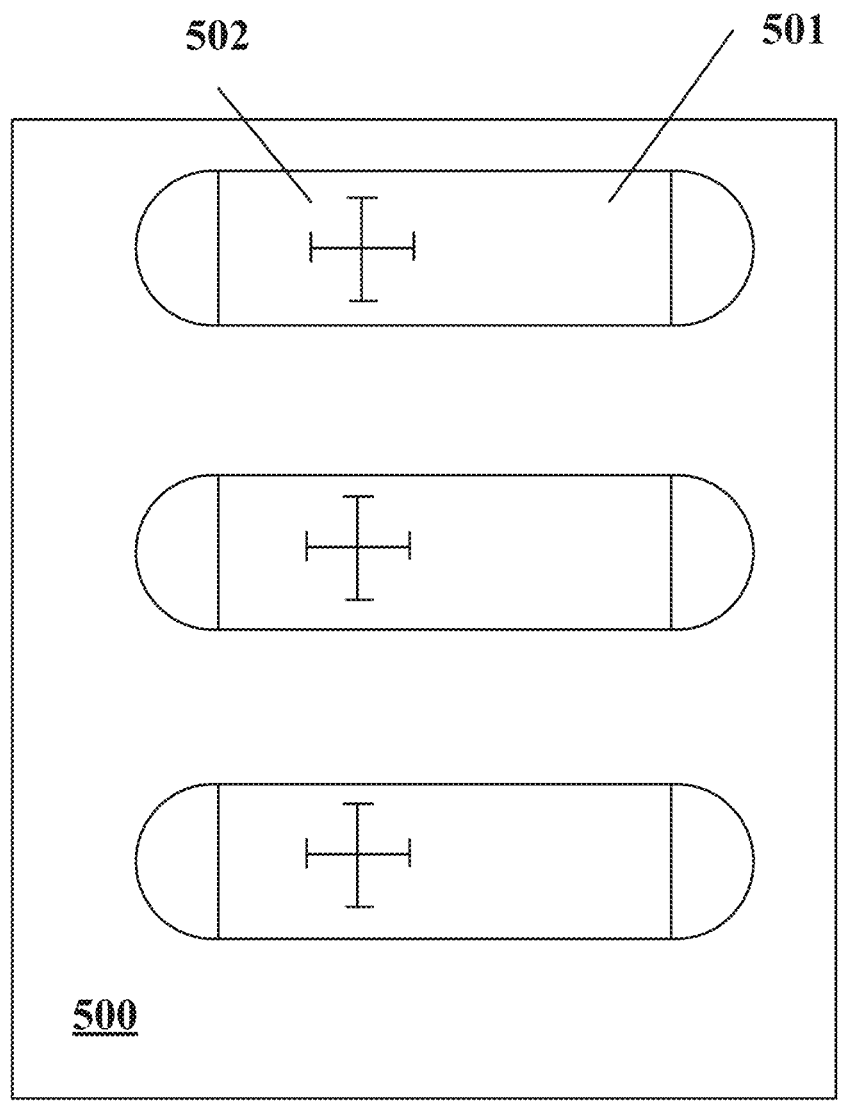
FIG. 5 is another schematic diagram illustrating a sample plate according to some embodiments of the present disclosure.

FIG. 5 is another schematic diagram illustrating a sample plate 500 according to some embodiments of the present disclosure. As shown in FIG. 5, a sample plate 500 may include a plurality of sample cells 501. A cross-shaped scaling pattern 502 may be arranged at the bottom of each of the sample cells 501. The scaling pattern 502 may include two line segments perpendicular to each other, and lengths of the two line segments may be the same or different.

Using the scaling pattern 502 on the sample plate 500 of FIG. 5, the magnification of the microscopic device may also be determined from the digital image generated by the image sensor 101. For example, the magnification of the microscopic device may be determined based on the above formulas (1)-(2) and the length of any one of the two line segments in the scaling pattern 502. Alternatively, two magnifications may be determined respectively based on each of the two line segments, and then an average value of the two magnifications may be designated as the magnification of the microscopic device.

Figure 6A:
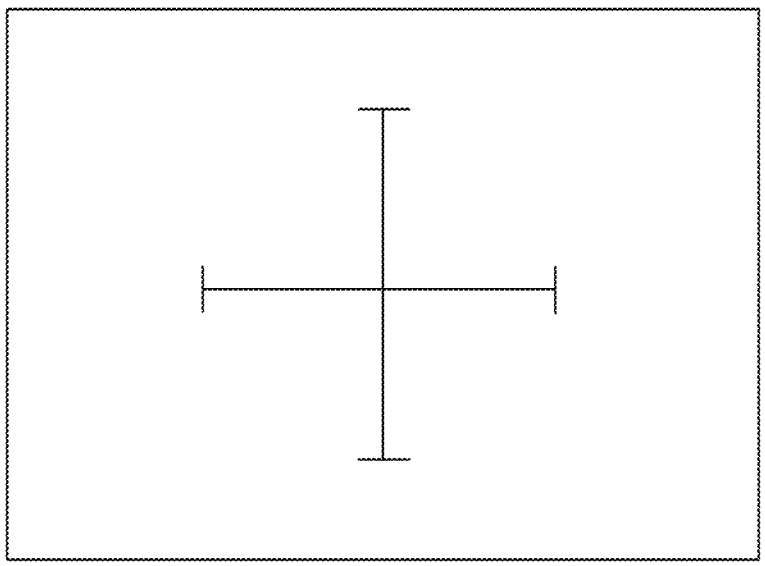
FIG. 6A is a schematic diagram illustrating a scaling pattern on a sample plate according to some embodiments of the present disclosure.
Figure 6B:
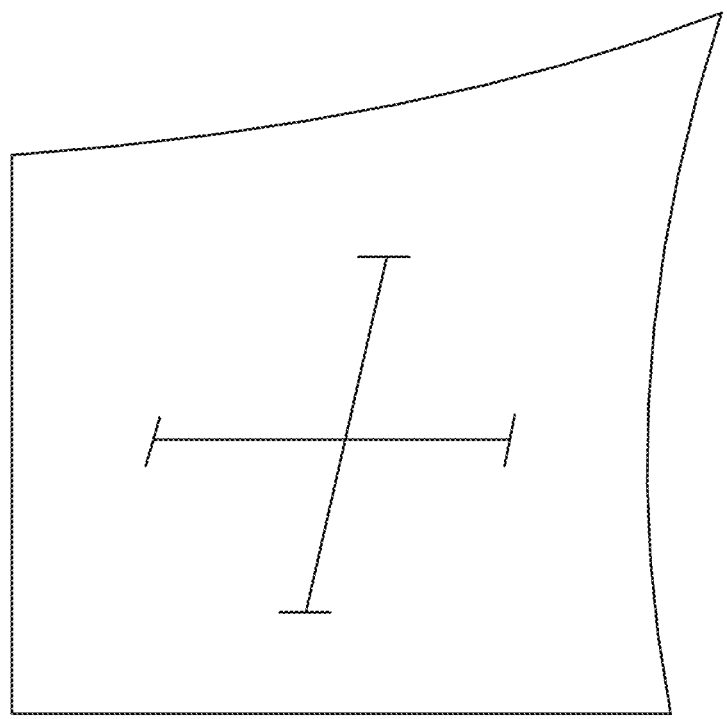
FIG. 6B is a schematic diagram illustrating an image of the scaling pattern on a sample plate according to some embodiments of the present disclosure.

In addition, the scaling pattern 502 on the sample plate 500 of FIG. 5 may also be used for identifying and correcting a distortion of the microscopic device 100. For example, when there is no distortion in the optical imaging device 104 of the microscope device 100, an image of the scaling pattern 502 should also be two line segments perpendicular to each other, as shown in FIG. 6A. However, if there is a distortion in the optical imaging device 104 of the microscope device 100, the two line segments in the image of the scaling pattern 502 may no longer be vertical, as shown in FIG. 6B. Based on the image of the two line segments, the processor 103 may recognize the distortion of the optical imaging device of the microscope device 100. Further, the processor 103 may also correct the digital image generated by the image sensor 101 based on known parameters such as a size of the scaling pattern 502, to improve the image quality.

The sample plate according to the present disclosure and how to obtain the magnification of the microscopic device based on the scaling pattern on the sample plate are described above. It should be understood that the present disclosure may not be limited to the above embodiments.

Figure 7:
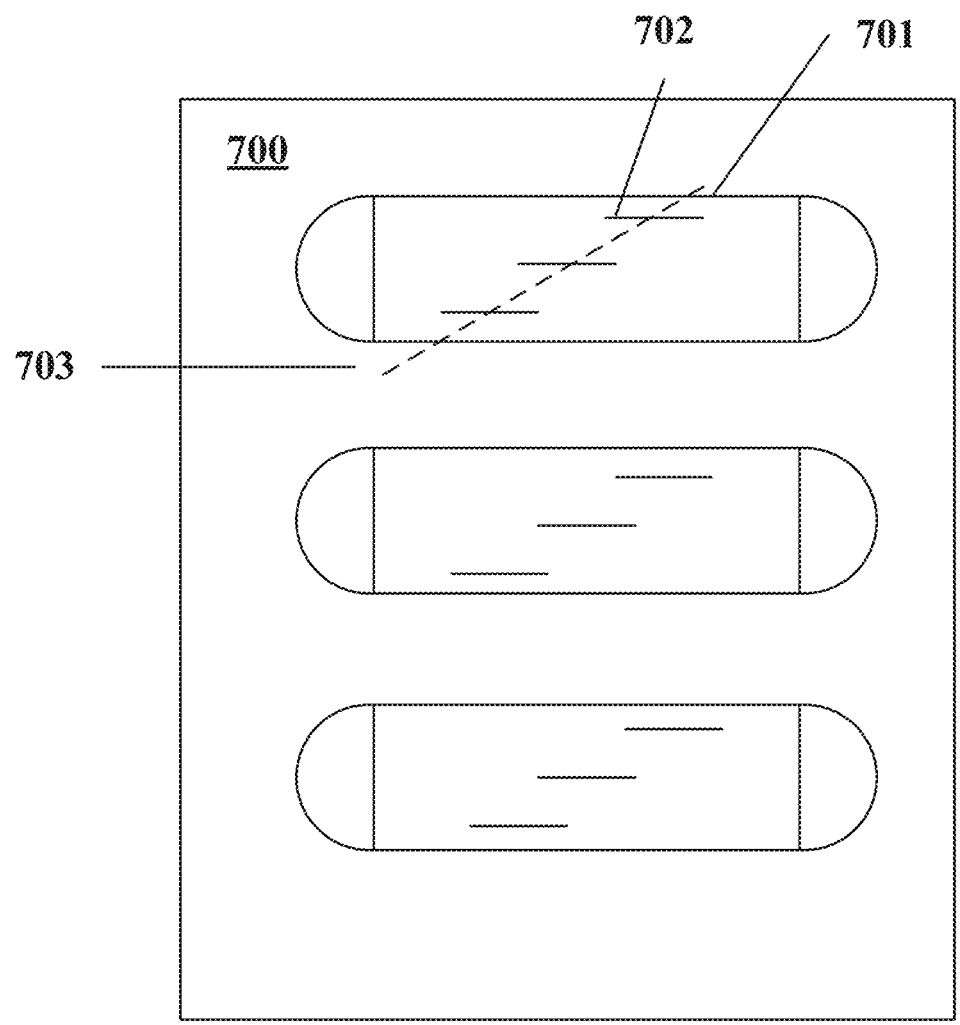
FIG. 7 is another schematic diagram illustrating a sample plate according to some embodiments of the present disclosure.

For example, FIG. 7 is another schematic diagram illustrating a sample plate 700 according to some embodiments of the present disclosure. As shown in FIG. 7, the sample plate 700 may include a plurality of sample cells 701 extending in a horizontal direction, and a scaling pattern 702 may be arranged at the bottom of each of the sample cells 701. The scaling pattern 702 may include a plurality of tick marks, each of the plurality of tick marks may extend in a horizontal direction (a first direction), and the plurality of tick marks may be arranged in the direction of a dotted line 703 (a second direction). The direction of the dotted line 703 is not a vertical direction perpendicular to the horizontal direction. In this way, the scaling pattern 702 may cover most of the area of the plurality of sample cells 701. When the magnification of the microscopic device 100 is large and the visual field may cover only a portion of the plurality of sample cells 701, this form of the scaling pattern 702 may ensure that at least one complete tick mark appears in the visual field. In this way, the magnification of the microscopic device may be accurately determined no matter where the sample is observed in the plurality of sample cells 701.

In addition, in some embodiments according to the present disclosure, the orientation of the sample plate and the plurality of sample cells may also be determined according to the scaling pattern on the sample plate. For example, the sample plate 300 shown in FIG. 3 may include a plurality of sample cells 301 arranged in a vertical direction, and each sample cell 301 may extend in a horizontal direction.

When observing and photographing samples in the plurality of sample cells 301 through the microscope device 100, it may be impossible to observe and photograph all the samples in the plurality of sample cells 301 at the same time due to the visual field and other reasons. Therefore, it is necessary to move the sample table 105 so that the sample plate is moved in the visual field, to observe and photograph different sample cells 301 on the sample plate 300 or different portions of the same sample cell 301.

As shown in FIG. 3, each tick mark in the scaling pattern 302 may extend in the horizontal direction, that is, an extension direction of a tick mark may be the same as the arrangement direction of the sample cell, and the arrangement directions of the plurality of tick marks may be the same as the arrangement directions of the plurality of sample cells. Therefore, although only a portion of the plurality of sample cells may be displayed in the visual field or the image captured by the microscopic device, to perform an operation of observing and photographing different sample cells 301 or different areas of the same sample cell 301, the processor 103 or the operator may determine the extension directions and arrangement directions of the plurality of sample cells based on the extension directions and arrangement directions of the plurality of the tick marks, and move the sample plate 300 on the sample table 105 based on the determined extension directions and arrangement directions of the plurality of sample cells.

Figure 8:
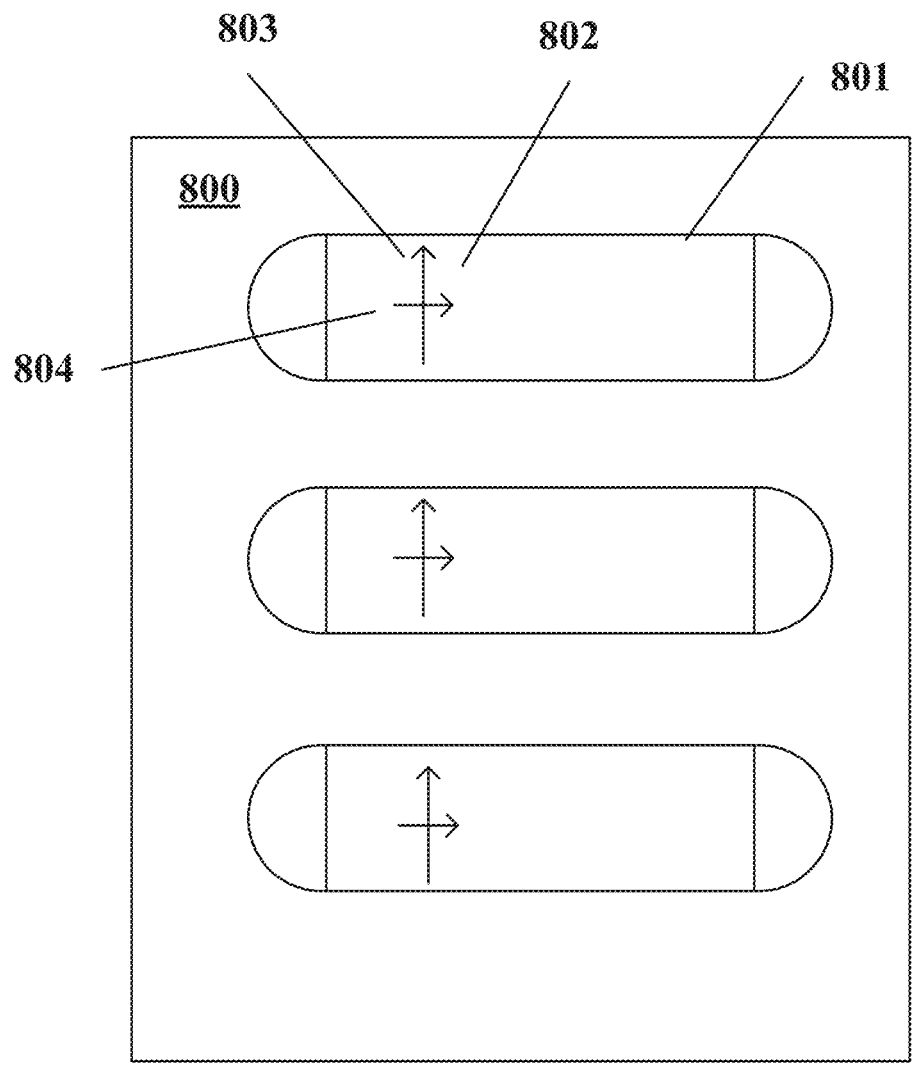
FIG. 8 is another schematic diagram illustrating a sample plate according to some embodiments of the present disclosure.

FIG. 8 is another schematic diagram illustrating a sample plate 800 according to some embodiments of the present disclosure. As shown in FIG. 8, the sample plate 800 may include a plurality of sample cells 801 extending in the horizontal direction, and the plurality of sample cells 801 may be arranged in the vertical direction. A scaling pattern 802 may be arranged at the bottom of each of the plurality of sample cells 801. The scaling pattern 802 may include a first mark for determining an arrangement direction and an extension direction of a sample cell 801. The first mark may be composed of two arrows 803 and 804 perpendicular to each other, wherein the arrow 803 may extend in the vertical direction and the arrow 804 may extend in the horizontal direction. In addition, in the example, the longer arrow may indicate the arrangement direction of the sample cell, and the shorter arrow may indicate the extension direction of the sample cell. As shown in FIG. 8, a length of the arrow 803 may be greater than a length of the arrow 804. Therefore, a plurality of sample cells 801 being arranged in the vertical direction may be determined based on the extension direction of the arrow 803, and the sample cell 801 extending in the horizontal direction may be determined based on the extension direction of the arrow 804.

Figure 9:
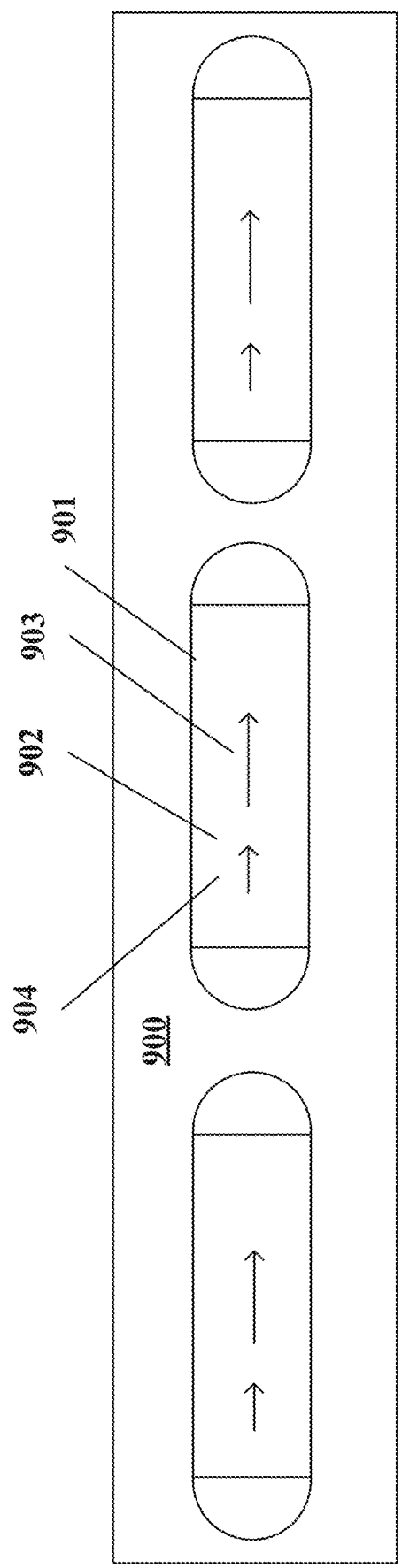
FIG. 9 is another schematic diagram illustrating a sample plate according to some embodiments of the present disclosure.

FIG. 9 is another schematic diagram illustrating a sample plate 900 according to some embodiments of the present disclosure. As shown in FIG. 9, the sample plate 900 may include a plurality of sample cells 901 arranged in the horizontal direction, and each of the plurality of sample cells 901 may extend in the horizontal direction. A scaling pattern 902 may be arranged at the bottom of each sample cell 901. The scaling pattern 902 may include a first mark for determining an arrangement direction and an extension direction of a sample cell 901. The first mark may be composed of arrows 903 and 904, wherein the longer arrow 903 may indicate the arrangement direction of the sample cell 901, and the shorter arrow 904 may indicate the extension direction of the sample cell 901. In this way, through the extension direction of arrows 903 and 904, the plurality of sample cells 901 arranged in the horizontal direction may be determined, and each sample cell 901 extending in the horizontal direction may also be determined.

Figure 10:
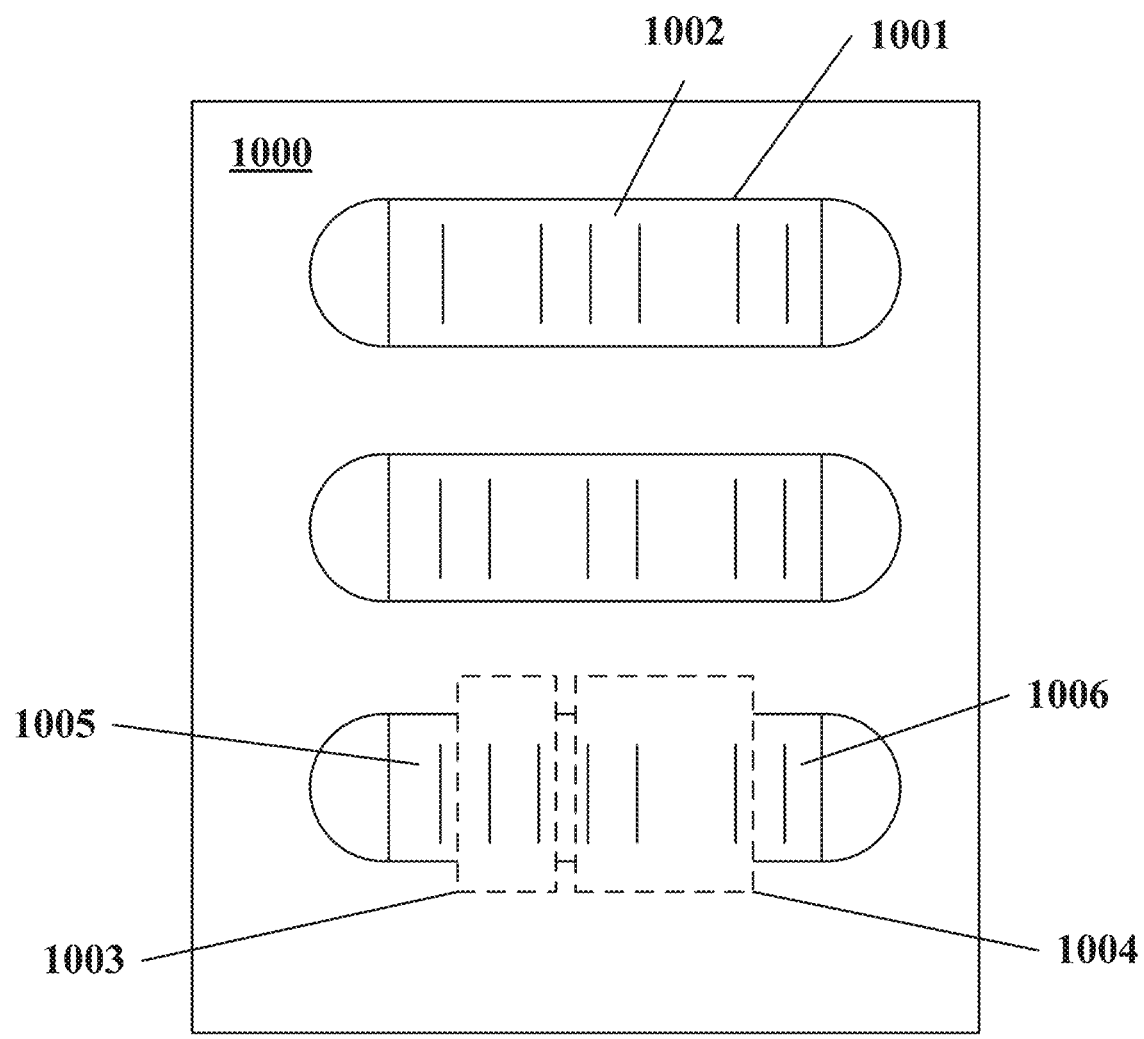
FIG. 10 is another schematic diagram illustrating a sample plate according to some embodiments of the present disclosure.

FIG. 10 is another schematic diagram illustrating a sample plate 1000 according to some embodiments of the present disclosure. As shown in FIG. 10, the sample plate 1000 may include a plurality of sample cells 1001 arranged in a vertical direction, and each of the plurality of the sample cells 1001 may extend in the horizontal direction. A scaling pattern 1002 may be arranged at the bottom of a sample cell 1001. The scaling pattern 1002 may include a second mark 1004 for identifying the sample plate and a third mark 1003 for identifying the sample cell. The second mark 1004 and the third mark 1003 may be composed of a plurality of tick marks, which may be arranged in the horizontal direction, and each of the plurality of the tick marks may extend in the vertical direction. The leftmost tick mark 1005 and the rightmost tick mark 1006 may represent a beginning and an end of the second mark 1004 and the third identification 1003. The second mark 1004 and the third mark 1003 may be between the tick mark 1005 and the tick mark 1006. A serial number of the sample plate and a serial number of the sample cell may be determined respectively based on the second mark 1004 and the third mark 1003.

As shown in FIG. 10, in the lower sample cell 1001, the third mark 1003 includes two tick marks, and the serial number of the sample cell where the third mark 1003 is located is determined as 11. In the upper sample cell 1001, the third mark 1003 includes a tick mark, and based on spacing between the tick marks, a tick mark is missed in front of this tick mark. Therefore, the serial number of the sample cell where the third mark 1003 is located may be determined as 01. Similarly, for the third mark 1003 in the middle sample cell 1001, the serial number of the sample cell may be determined as 10.

Similarly, in the second mark 1004, based on the spacing between the tick marks, a missing tick mark may represent 0, and then the serial number of the sample plate 1000 may be determined as 1101.

Figure 11:
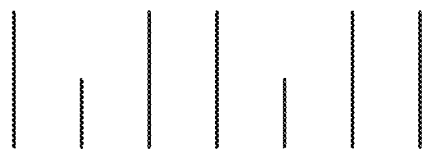
FIG. 11 is a schematic diagram illustrating a set of tick marks of the scaling pattern on the sample plate according to some embodiments of the present disclosure.

In addition, in some embodiments of the present disclosure, other ways may also be used to represent a number 0 or 1. For example, in a set of tick marks as shown in FIG. 11, 0 and 1 may be represented by tick marks of different lengths. The longer tick mark may represent 1 and the shorter tick mark may represent 0. The set of tick marks in FIG. 11 may be determined as 1011.

It should be understood that under the instruction and enlightenment of the present disclosure, those skilled in the art may combine the first mark, the second mark, the third mark, and the tick mark in other ways as a scaling pattern.

Figure 12:
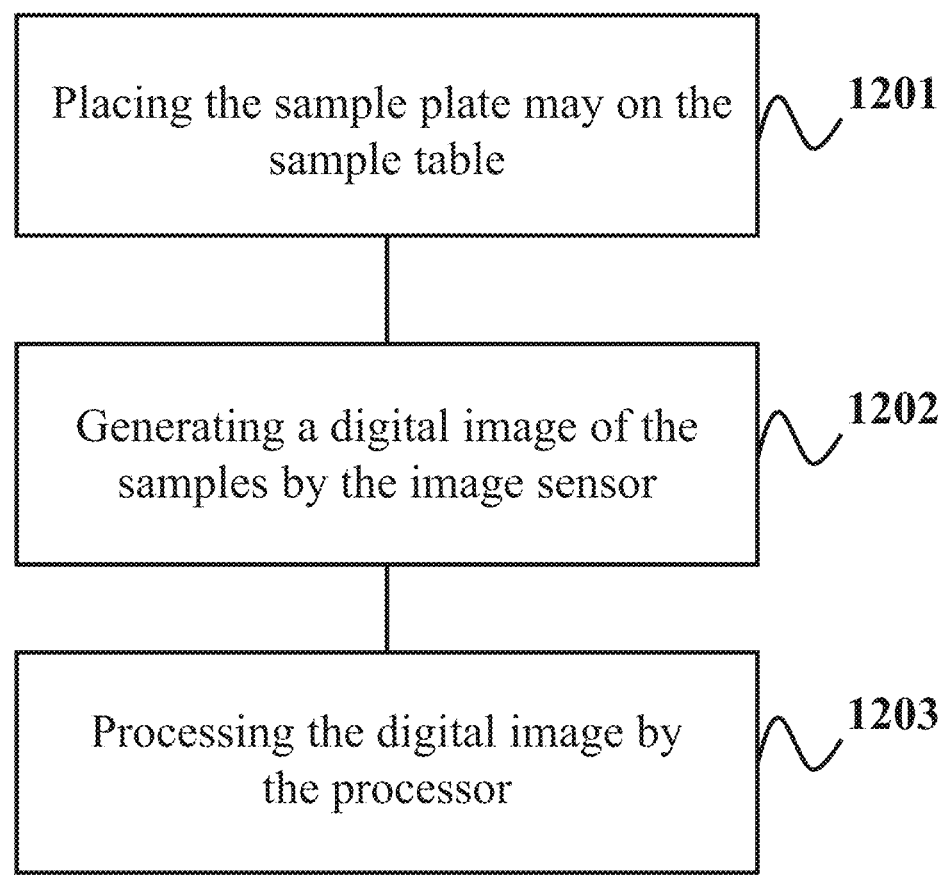
FIG. 12 is a flowchart illustrating a process for operating the microscopic device according to some embodiments of the present disclosure.

FIG. 12 is a flowchart illustrating a process for operating the microscopic device 100 according to some embodiments of the present disclosure.

As shown in FIG. 12, the sample plate may be placed on the sample table 105 (operation 1201). Samples to be observed and captured may be located in the sample cells of the sample plate.

Then, a digital image of the samples may be generated by the image sensor 101 (operation 1202). The optical image generated by the optical imaging device 104 of the microscopic device 100 may be received by the image sensor 101 and the digital image may be generated. The digital image may be stored in the memory 102.

Then, the processor 103 may read the digital image from the memory 102 and perform various processes (operation 1203). For example, as described above, based on the scaling pattern in the digital image, the magnification of the microscopic device 100 may be determined; the extension direction and arrangement direction of the sample cell may be determined; the (serial number of) sample plate may be determined; or the (serial number of) sample cell may be determined, or the like.

Figure 14:
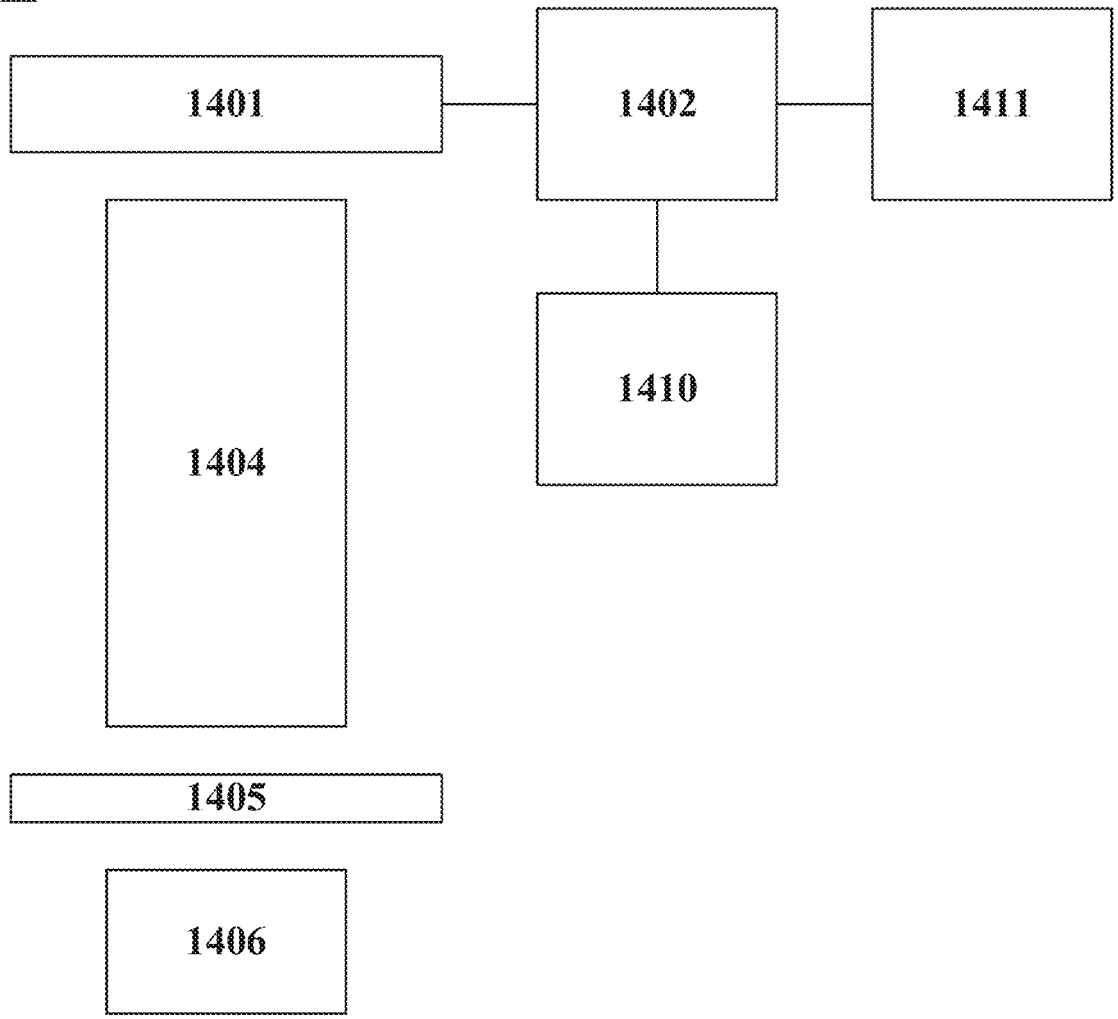
FIG. 14 is another schematic diagram illustrating a microscopic device according to some embodiments of the present disclosure.

FIG. 14 is another schematic diagram illustrating a microscopic device according to some embodiments of the present disclosure. As shown in FIG. 14, a microscopic device 1400 may be an optical microscopic device, including an image sensor 1401, a memory 1402, a transmission device 1411, an inputting device 1410, an optical imaging device 1404, a sample table 1405, and a light source 1406. The image sensor 1401, the optical imaging device 1404, the sample table 1405, and the light source 1406 may be similar to the corresponding devices in the microscopic device 100 shown in FIG. 1, so a detailed description may not be repeated herein.

For example, the sample plate with the scaling pattern may be arranged on the sample table 1405, and the optical imaging device 1404 may generate an optical image of samples. In addition, the scaling pattern in the sample plate may also be included in the optical image. As described above, the scaling pattern may be configured to determine the magnification of the microscopic device, determine the direction of the sample plate, identify the sample plate or sample cell, or the like. The image sensor 1401 may convert an optical image into a digital image.

In addition, a user of the microscope device 1400 may input information about the scaling pattern (i.e., pattern information) by the inputting device 1410. The pattern information may include size information of the scaling pattern. For example, when the scaling pattern is the scaling pattern 202 shown in FIG. 2, the pattern information may include information about the length L of the line segment. When the scaling pattern is the scaling pattern 302 shown in FIG. 3, the pattern information may include the information of the spacing D of the tick mark.

In addition, the pattern information may include an identifier of the scaling pattern. For example, the user may input a unique serial number of the scaling pattern by the inputting device 1410. The serial number of the scaling pattern may be stored in a database in association with relevant information of the scaling pattern. Based on the serial number, the scaling pattern corresponding to the serial number and the relevant information of the scaling pattern, such as size, spacing, etc., may be found in the database.

In some illustrative embodiments, a type of the sample plate may also be determined by the unique serial number of the scaling pattern. For example, in the database, the serial number of the scaling pattern may also be stored in association with relevant parameters of the sample plate. For example, the relevant parameters of the sample plate may include: the type of the sample plate, the numbers of sample cells, the depth of sample cells, or the like.

In addition, the user may also input information about the sample (first sample information) by the inputting device 1410. For example, the information may include the type of sample. In this way, based on the information about the sample, the type of the samples such as red blood cells, yeast, algae, etc., may be determined.

The transmission device 1411 may transmit the digital image to other devices. For example, the transmission device 1411 may transmit the digital image to a remote server, such as a cloud server or the like. The server may include an image processing device to further process the received image.

Figure 19:
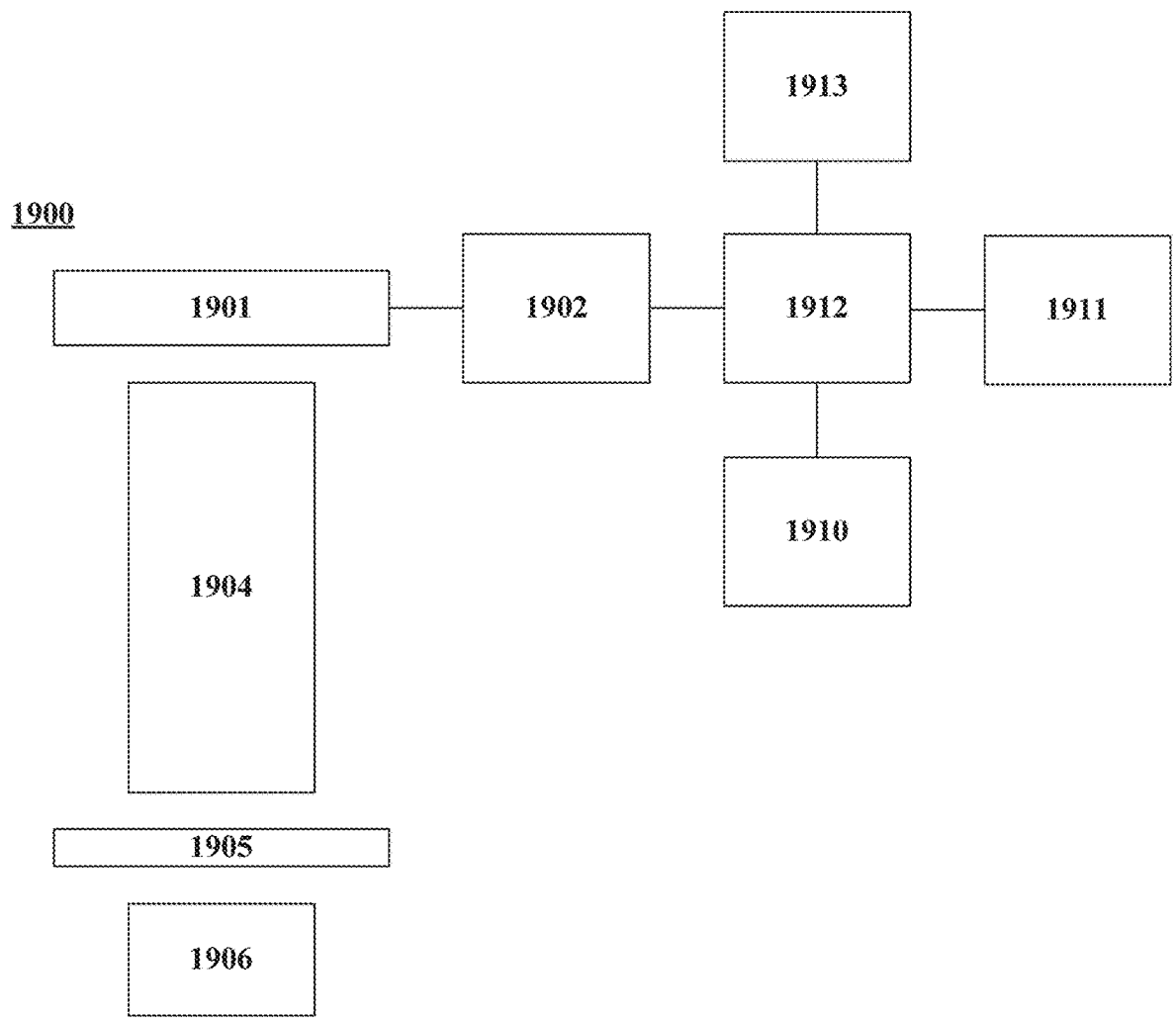
FIG. 19 is another schematic diagram illustrating a microscopic device according to some embodiments of the present disclosure.

FIG. 19 is another schematic diagram illustrating a microscopic device according to some embodiments of the present disclosure. As shown in FIG. 19, the microscopic device 1900 may include an image sensor 1901, a memory 1902, a transmission device 1911, an inputting device 1910, an optical imaging device 1904, a sample table 1905, and a light source 1906. These components are similar to the corresponding components of the microscopic device 1400 shown in FIG. 14, and may not be repeated herein. In addition, as shown in FIG. 19, the microscopic device 1900 may also include a controller 1912 and a receiving device 1913. The receiving device 1913 may receive information transmitted by external devices, and the controller 1912 may control the operation of the microscopic device 1900 based on the information. In some embodiments according to the present disclosure, the user may interact with the microscopic device 1900 by a mobile device (e.g., a mobile phone, tablet, laptop, etc.). For example, the microscopic device 1900 may transmit a captured microscopic image to the mobile device and display the microscopic image on the mobile device. The user may adjust a photographing parameter (such as magnification, observation area, etc.) of the microscopic device 1900 based on a captured microscopic image, and transmit the photographing parameter to the microscopic device 1900 by the mobile device. Then, the microscopic device 1900 may adjust based on the photographing parameter included in the information transmitted by the mobile device, re-capture the microscopic image, and transmit the new microscopic image to the mobile device.

In addition, an interaction between the microscopic device 1900 and the mobile device may be carried out directly or indirectly through, for example, a cloud server, which may not be limited by the present disclosure.

Figure 15:
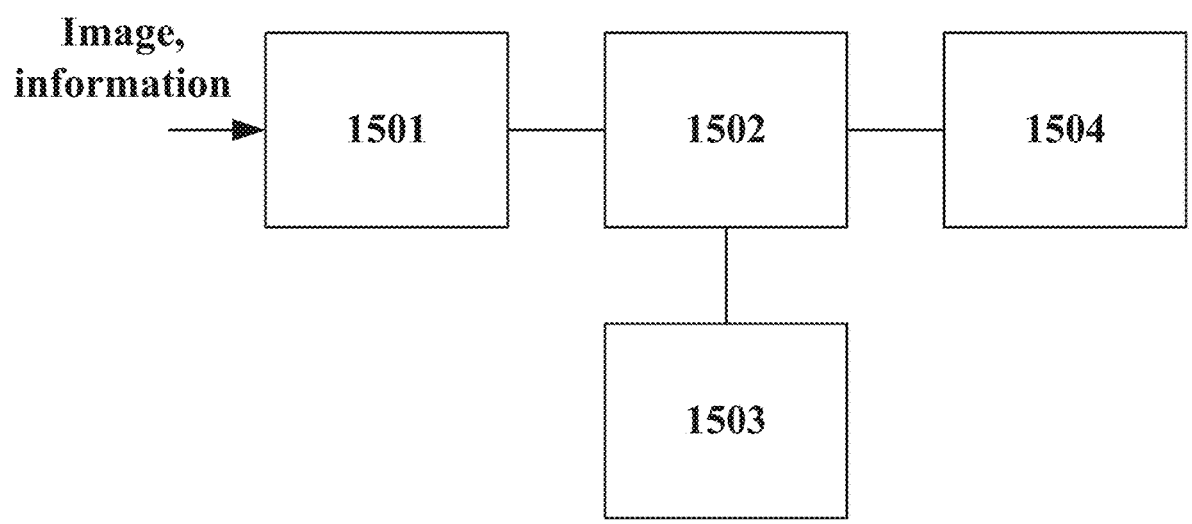
FIG. 15 is a schematic diagram illustrating an image processing device according to some embodiments of the present disclosure.

FIG. 15 is a schematic diagram illustrating an image processing device according to some embodiments of the present disclosure. As shown in FIG. 15, an image processing device 1500 may include a receiving device 1501, a storage device 1502, a processor 1503, and a transmission device 1504.

The receiving device 1501 may receive a digital image captured by the above-mentioned microscopic device according to the present disclosure. A scaling pattern may be included in the digital image.

In addition, in some embodiments according to the present disclosure, the receiving device 1501 may also receive pattern information and/or first sample information related to the digital image.

The storage device 1502 may store the digital image and various information received by the receiving device 1501.

The processor 1503 may obtain the digital image and various information from the storage device 1502 and process the digital image. For example, the processor 1503 may determine the magnification of the microscopic device based on the scaling pattern in the digital image.

The transmission device 1504 may transmit the digital image and information related to the digital image (e.g., the magnification, etc.) to, for example, a mobile device or the like.

In some embodiments according to the present disclosure, since specifications of the sample plates may be different, the parameters such as the length and/or spacing of the tick marks of the scaling pattern on the sample plates with different specifications may be different. In this case, the processor 1503 may also need to further combine the pattern information related to the digital image to determine the magnification of the microscopic device.

In addition, in some embodiments according to the present disclosure, the processor 1503 may also determine the direction of the sample plate where the sample is located based on the pattern information. For example, when the sample plate is the sample plate 900 shown in FIG. 9, the pattern information may indicate that the direction of the arrow is the same as the longitudinal direction of the sample plate 900. In this way, the processor 1503 may recognize the direction of the arrow of the scaling pattern from the digital image, and designate the direction of the arrow as the longitudinal direction of the sample plate.

Further, in some embodiments according to the present disclosure, the processor 1503 may classify digital images based on pattern information. For example, the digital images may be classified based on the size of the scaling pattern, and digital images with the same size of the scaling pattern may be divided into a group. When browsing the group of digital images later, the digital images may be scaled to make the size of the scaling pattern the same, so that users may intuitively observe and compare the relative size of the samples in each digital image.

Figure 16:
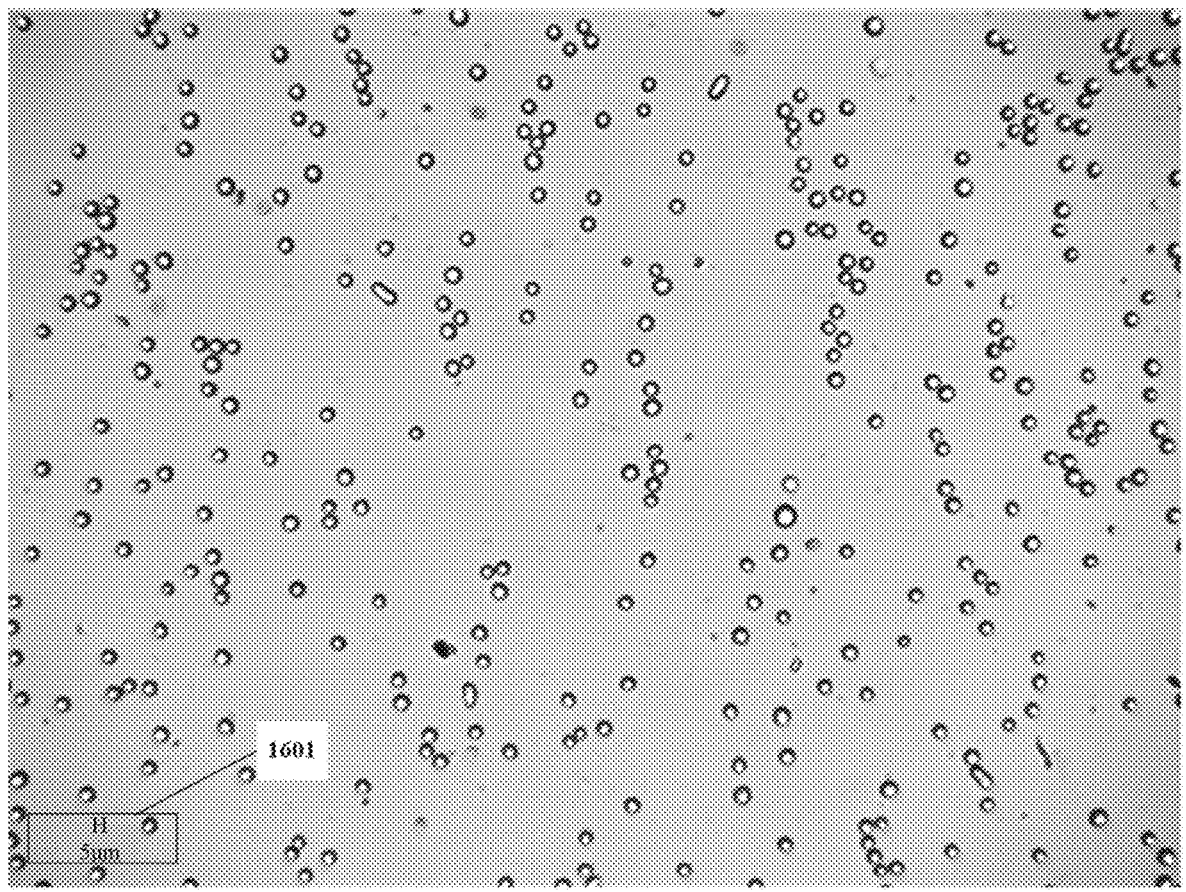
FIG. 16 is a schematic diagram illustrating a microscopic image according to some embodiments of the present disclosure.

Further, in some embodiments according to the present disclosure, the processor 1503 may generate a first image from the pattern information and integrate the first image into the digital image. For example, as shown in FIG. 16, for the sample plate shown in FIG. 2, the processor 1503 may obtain that the length L of the tick mark is 5 μm based on the pattern information. The processor 1503 may generate a message with the word "5 μm," and the first image may be integrated into the digital image. In the synthesized digital image, the value of the length L of the tick mark may be marked near the tick mark, so that the user may more intuitively understand the size of the sample when browsing the digital image.

In addition, the processor 1503 may classify the digital images based on the first sample information. For example, when the first sample information includes the type of the samples, the processor 1503 may determine that the digital images of samples of the same type belong to the same group.

In addition, in some embodiments according to the present disclosure, the first sample information may also include other information such as production date, photographing date, source, copyright information, or the like. The processor 1503 may also divide the digital images with the same date into a group.

Figure 17:
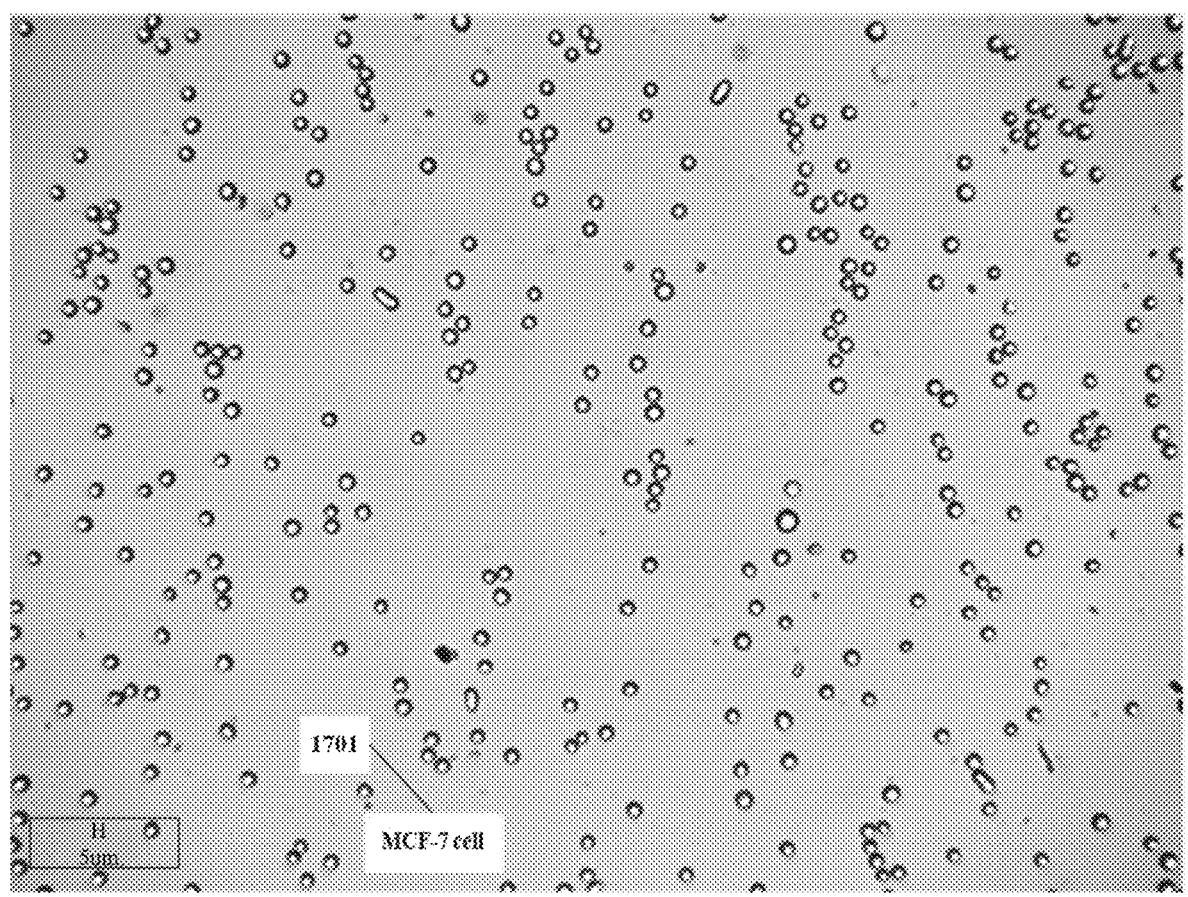
FIG. 17 is another schematic diagram illustrating a microscopic image according to some embodiments of the present disclosure.

In some embodiments according to the present disclosure, the processor 1503 may generate a second image based on the first sample information and integrate the second image into the digital image. As shown in FIG. 17, when the first sample information indicates that the type of the samples is human breast cancer cells (MCF-7 cells), the processor 1503 may generate a second image 1701 including the word "MCF-7 cells" and integrate the image 1701 into the digital image. In this way, when the digital image is displayed on a display, for example, the type of the sample may be directly known.

In some embodiments according to the present disclosure, a client may find and download the digital image from the server. For example, the client may enter a keyword, such as yeast cells, and the keyword may be transmitted to a remote server. The server may find digital images of yeast cells in all sample information in the database based on the keyword, and provide a list or thumbnails of these digital images to the client. The client may select and download a selected digital image and related information of the selected digital image based on the information provided by the server. Further, in some embodiments according to the present disclosure, the client may pay a fee to the server to obtain a license to use the selected digital image. After the server determines that the client has obtained the license, the selected digital image may be transmitted to the client.

Further, in some embodiments according to the present disclosure, the processor 1503 may analyze the digital image based on the scaling pattern to obtain second sample information related to the sample. The second sample information may include, for example, diameters of the samples, values of major axis and values of minor axis of the samples, a size of the visual field, a concentration of the samples and other information.

Figure 18:
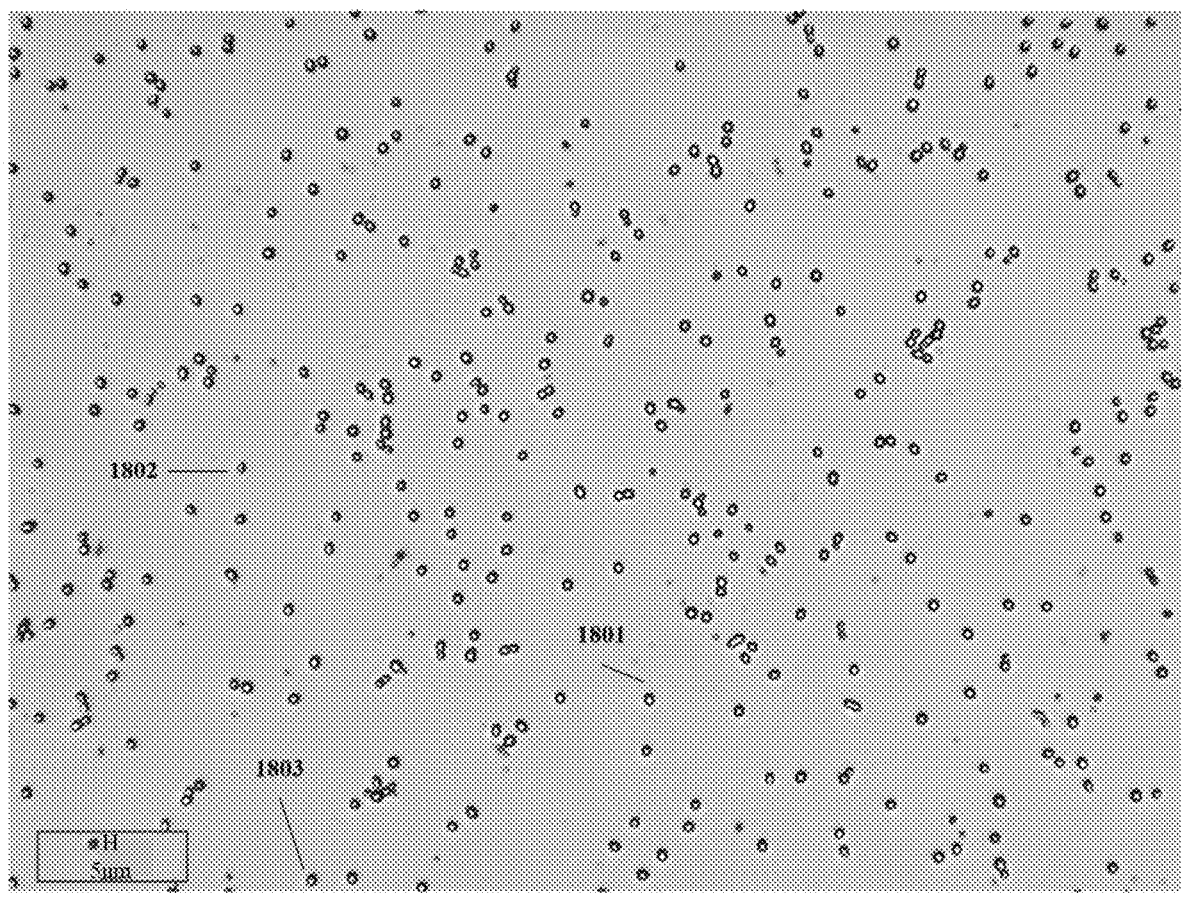
FIG. 18 is another schematic diagram illustrating a microscopic image according to some embodiments of the present disclosure.

For example, FIG. 18 is another schematic diagram illustrating a microscopic image according to some embodiments of the present disclosure. As shown in FIG. 18, based on the pattern information, the processor 1503 may determine that the length unit of the scaling pattern in the digital image is 5 μm. Based on a determination that the length unit of the scaling pattern in the digital image is 5 μm, the magnification of the digital image in FIG. 18 may be determined as 9.8. Based on the first sample information, the processor 1503 may further determine that the type of sample in the digital image is yeast cells. Based on the information that the type of sample in the digital image is yeast cells, the processor 1503 may perform an image recognition operation on identifying yeast cells. For example, the processor 1503 may determine a yeast cell 1802 based on the image recognition operation and determine that the diameter of the yeast cell 1802 is 6 μm based on the scaling pattern, the diameter of the yeast cell 1802 may be stored in the second sample information.

Further, in some embodiments according to the present disclosure, the processor 1503 may determine a plurality of yeast cells by the image recognition operation and determine the diameter of each of the plurality of the yeast cells based on the scaling pattern. Then, the processor 1503 may store an average value of the diameters of the plurality of yeast cells in the second sample information as a diameter of the plurality of yeast cells.

For example, as shown in FIG. 18, the processor 1503 may identify yeast cells 1801, 1802, and 1803 from a digital image. Based on the scaling pattern, the diameter of these yeast cells may be determined as 9 μm, 6 μm, and 9 μm. The average value of the diameters is 8 μm. The processor 1503 may store the average value in the second sample information as the diameter value of the samples.

In addition, in some embodiments according to the present disclosure, the processor 1503 may identify 393 yeast cells from the digital image and determine the diameter of each of the 393 yeast cells, so that the average value of the diameters of the 393 yeast cells may also be obtained and stored in the second sample information.

In addition, the processor 1503 may also determine the size of a visual field of photographing and the concentration of the samples from the digital image. As shown in FIG. 18, the processor 1503 may determine that the area of the sample plate in the digital image is 0.46×0.35 mm² based on the scaling pattern. In addition, as described above, the type of sample plate may also be determined based on the scaling pattern, so that the depth of the sample cell may be obtained as 0.5 μm. In this way, the processor 1503 may determine that the concentration of yeast cells is about 5×10⁶/ml.

Figure 20:
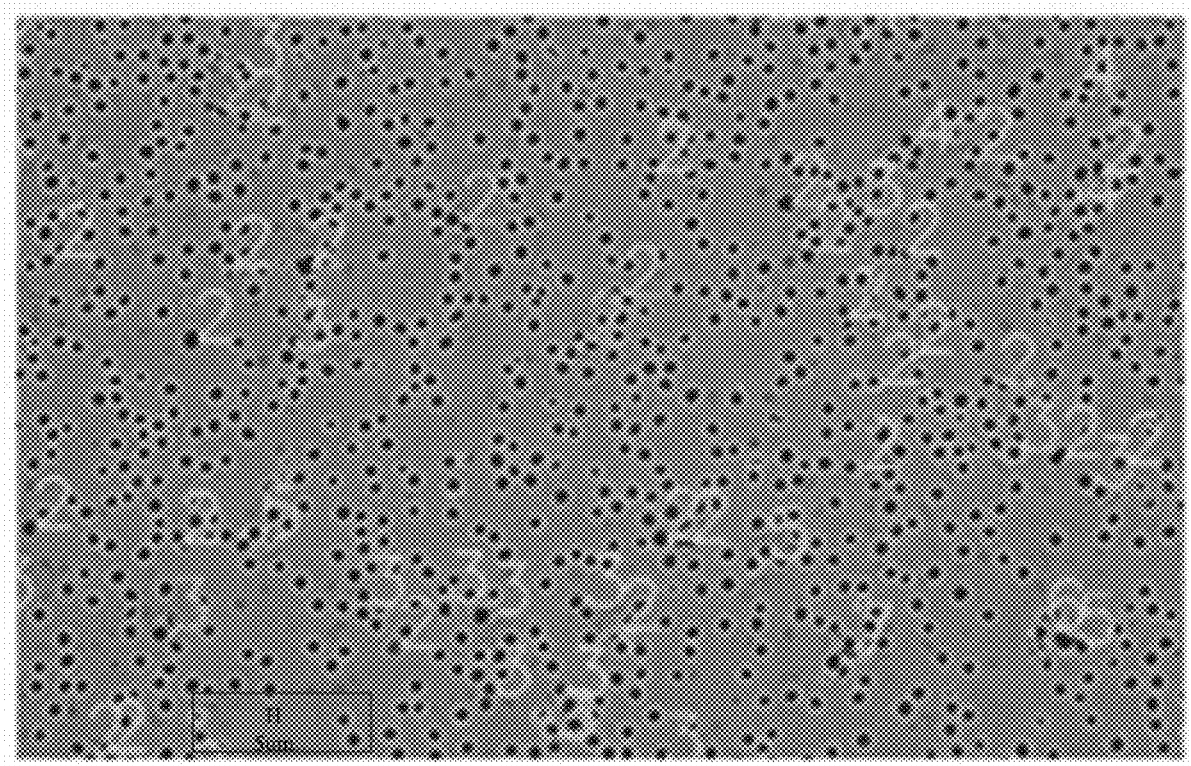
FIG. 20 is another schematic diagram illustrating a microscopic image according to some embodiments of the present disclosure.

In addition, the processor 1503 may determine the value of the major axis and the value of the minor axis of the sample from the digital image. For example, FIG. 20 is another schematic diagram illustrating a microscopic image of *chlorella* according to some embodiments of the present disclosure. The processor 1503 may determine the value of the major axis and the value of the minor axis of each *chlorella* based on the scaling pattern in FIG. 20, and further determine that the average value of the minor axis of the *chlorella* is about 17.66 µm, and the value of the major axis of the *chlorella* is about 19.11 µm.

Figure 21:
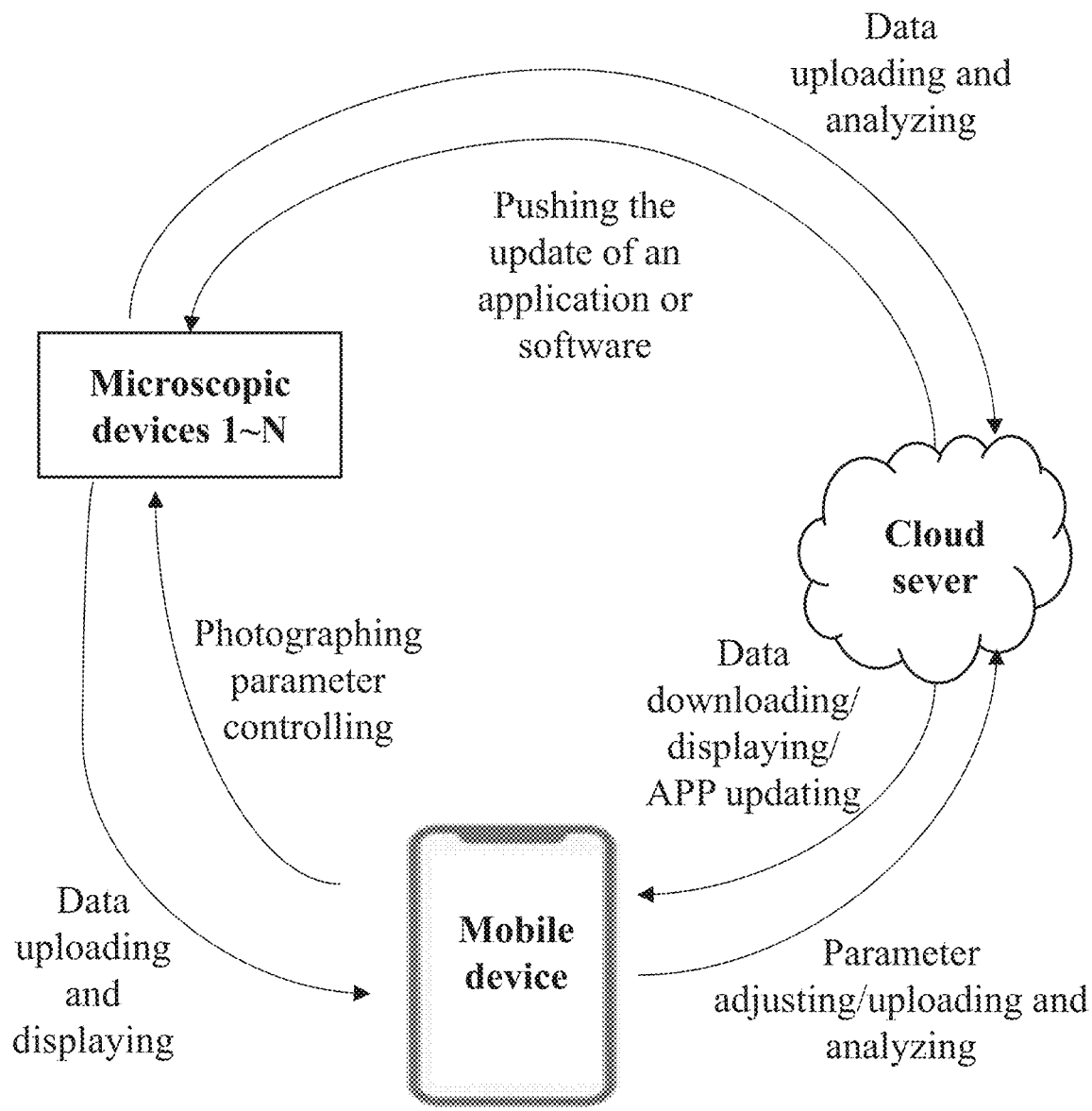
FIG. 21 is a schematic diagram illustrating a microscopic analysis system according to some embodiments of the present disclosure.

According to the embodiment of the present disclosure, a microscopic analysis system is also provided, including the microscopic device, the image processing device, the mobile device, etc. It should be understood that the image processing device of the present disclosure may be a single server or multiple servers, or a cloud server. As shown in FIG. 21, the mobile device may control the microscopic device by the cloud server (for example, adjusting the photographing parameter, etc.), or receive the microscopic image captured by the microscopic device by the cloud server. The cloud server may transmit an update of an application to the microscopic device and/or the mobile device. In addition, a plurality of microscopic devices 1~N may be connected to the cloud server at the same time. The mobile device may browse the image captured by a specified microscopic device or control the operation of the microscopic device as needed. The cloud server may store and analyze microscopic images captured by the plurality of microscopic devices, and may transmit the microscopic images and an analysis result to the mobile device.

In each of the above embodiments, the scaling pattern is arranged in the sample plate. In some embodiments according to the present disclosure, the scaling pattern may be arranged in an optical imaging device of the microscopic device. For example, a transparent glass plate with a scaling pattern may be integrate to a lens group of the optical imaging device. In this way, the actual magnification of sample imaging may also be obtained based on a conversion of imaging magnification.

Further, in some embodiments according to the present disclosure, the sample may be yeast and the yeast may be counted.

Figure 22:
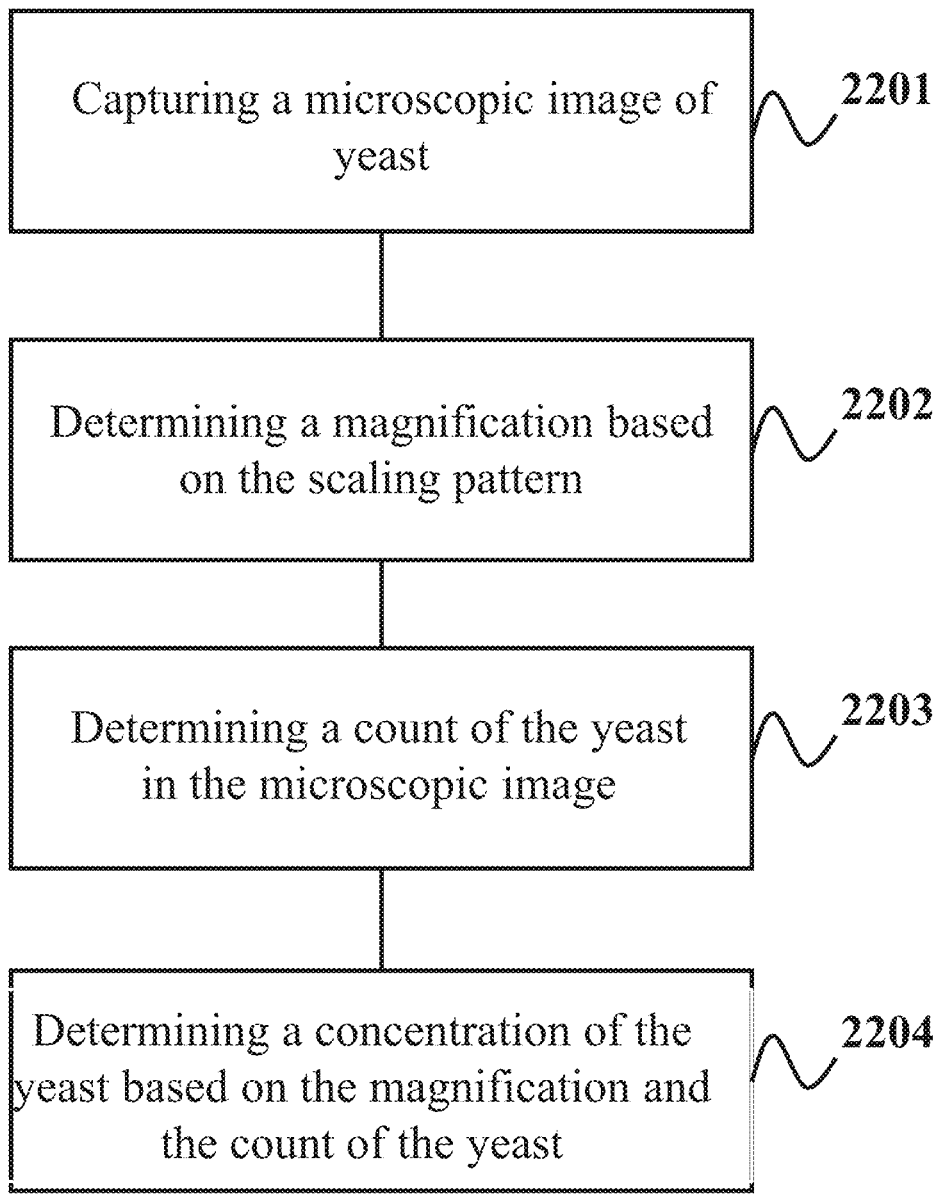
FIG. 22 is a flowchart illustrating a method for counting yeast according to some embodiments of the present disclosure.

FIG. 22 is a flowchart illustrating a method for counting yeast according to some embodiments of the present disclosure. As shown in FIG. 22, in the method, a microscopic image of yeast may be captured first, and the microscopic image may also include a scaling pattern for determining a magnification (operation 2201).

Then, the magnification may be determined based on the scaling pattern in the microscopic image (operation 2202).

Next, a count of the yeast in the microscopic image may be determined (operation 2203).

Finally, a concentration of the yeast may be determined based on the magnification and the count of the yeast (operation 2204).

The method for counting yeast according to the present disclosure may be described in further detail below in combination with embodiments.

The operation of photographing the yeast with a microscopic device is shown as follows.

Dyeing solution may be prepared first. Methylene violet or methylene blue may be used for dyeing. For example, 2% sodium citrate dihydrate methylene violet solution (including 0.01% methylene violet solution) may be prepared as follows: selecting 0.01 g methylene violet and 2 g trisodium citrate dihydrate, and then adding distilled water to make volume of the solution to 100 ml.

In an embodiment, 2% sodium citrate dihydrate methylene violet solution (including 0.01% methylene blue solution) may also be prepared as follows: selecting 0.01 g methylene blue and 2 g trisodium citrate dihydrate, and then adding distilled water to make volume of the solution to 100 ml.

Then, a sample of yeast may be taken. For yeast sludge or a sample having a high concentration of yeast, the sample may be diluted to a certain concentration range by using diluent.

Next, 1 ml of the sample of yeast may be mixed with 1 ml of the dyeing solution, and the mixed solution may be placed in a sample cell of the sample plate according to the above embodiments of the present disclosure.

Finally, the sample plate accommodating the sample may be placed on the sample table of the microscope device 100 and a microscopic image may be captured.

For example, FIG. 18 is another schematic diagram illustrating a microscopic image of the yeast captured by the microscope device according to some embodiments of the present disclosure.

The processor 103 of the microscopic device 100 may identify and determine the count of the yeast in the microscopic image based on an image identification algorithm stored in the memory 102. After identification and determination, the count of the yeast in the microscopic image may be determined as 393.

Further, the depth and/or width of the sample cell may be determined based on a type of sample plate. For example, the user may manually input the type of the sample plate to the microscope device 100. Based on the inputted type of the sample plate, the processor 103 of the microscopic device 100 may search size data in a database of the memory 102, such as the depth and/or width, or length of the sample cell based on the type of sample plate.

Further, in some embodiments according to the present disclosure, the processor 103 of the microscope device 100 may determine the type of sample plate based on the scaling pattern on the sample plate. For example, a sample plate may be the sample plate 1000 shown in FIG. 10. The scaling pattern 1002 on the sample plate 1000 may include a second mark 1004. The serial number of the sample plate may be determined based on the second mark 1004. The processor 103 may search the database of the memory 102 based on the serial number of the sample plate, so as to determine the type of sample plate and the depth and/or width, or length of the sample cell.

After determining the depth of the sample cell, the concentration of the sample of yeast may be determined. For example, in the microscopic image of the yeast shown in FIG. 19, the magnification may be determined as 9.8 based on the scaling pattern. It could be known that the area of the sample cell corresponding to the microscopic image is 0.46×0.35 mm$^2$. In addition, based on the type of the sample plate or the type of the sample cell inputted by the user, the processor 103 may search and determine the depth of the sample cell corresponding to the type of the sample plate or the type of the sample cell in the database of the memory 102. Therefore, the concentration of the sample of yeast may be $5\times10^6$/ml.

In addition, when the scaling pattern includes a third mark for identifying the sample cell, the processor 103 may also determine the type of the sample cell based on the third mark, and the size information such as the depth, width and length of the sample cell may be determined based on the type of the sample cell, and then volume of the sample cell may be determined.

In addition, the image processing device may also analyze the microscopic image of the yeast to obtain an analysis result. For example, the analysis results may include at least one of the following parameters: a concentration of alive yeast, a concentration of dead yeast, a total concentration of the yeast, a mortality rate of the yeast, a survival rate of the yeast, an average diameter of the yeast, an average circularity of the yeast, a bud rate of the yeast, or an aggregation rate.

Figure 29:
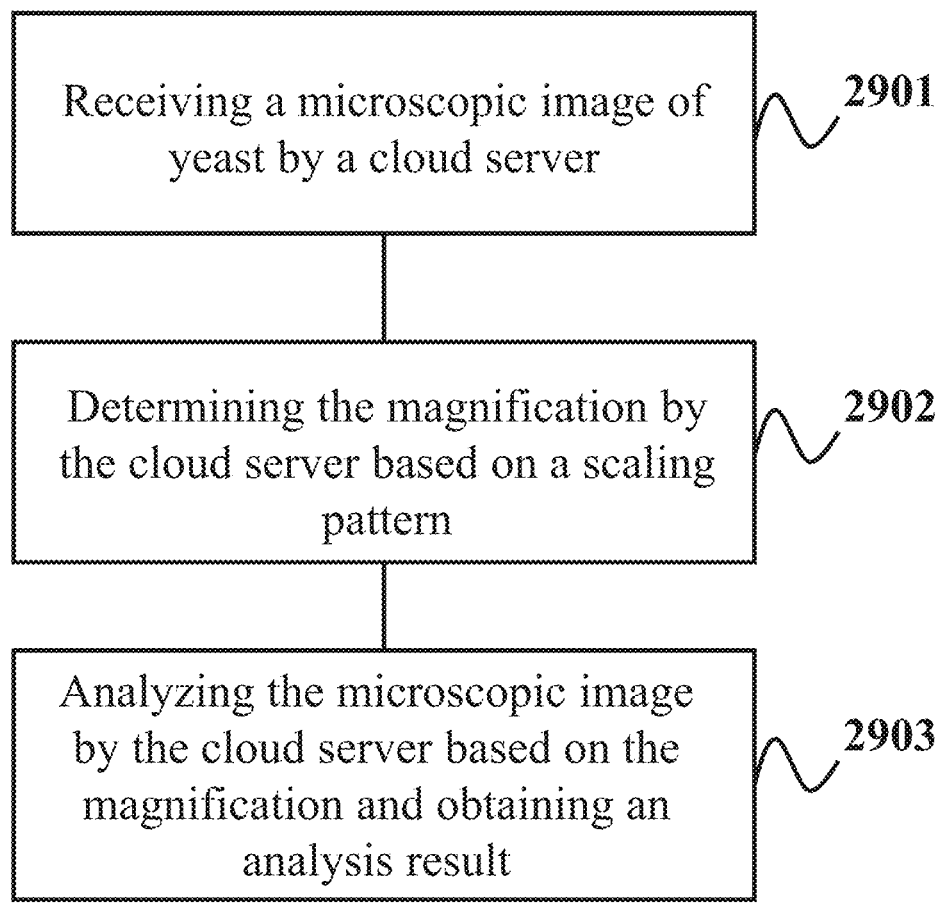
FIG. 29 is a flowchart illustrating a method for analysis of yeast according to some embodiments of the present disclosure.

FIG. 29 is a flowchart illustrating a method for analysis of yeast according to some embodiments of the present disclosure. As shown in FIG. 29, the method for analysis of yeast according to the embodiment of the present disclosure mainly includes the following operations:

A microscopic image of yeast may be received by a cloud server, wherein the microscopic image may also include a scaling pattern for determining a magnification (operation 2901);

The magnification may be determined by the cloud server based on the scaling pattern (operation 2902); and The microscopic image may be analyzed by the cloud server based on the magnification and an analysis result may be obtained (operation 2903).

Figure 23:
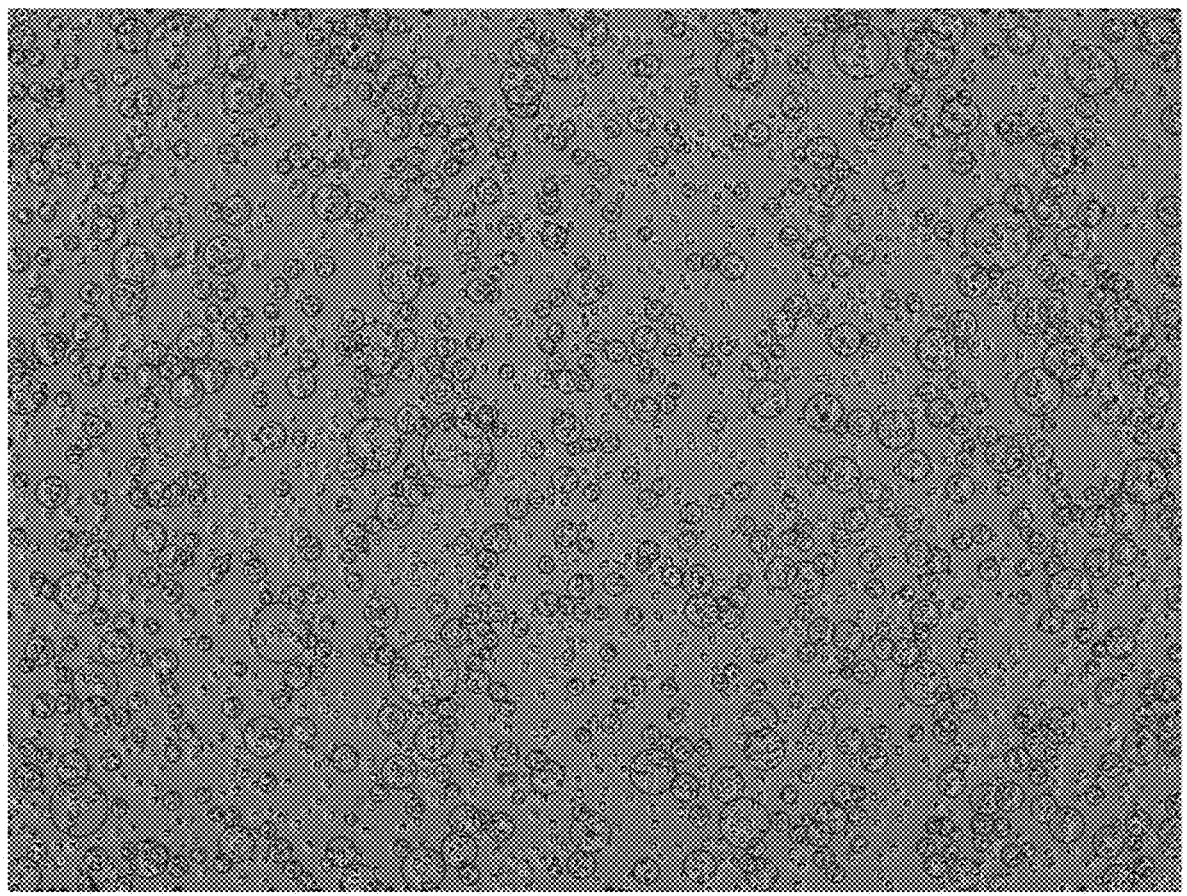
FIG. 23 is a schematic diagram illustrating a microscopic image of yeast according to some embodiments of the present disclosure.

For example, FIG. 23 is a schematic diagram illustrating a microscopic image of yeast captured by the microscopic device according to some embodiments of the present disclosure. Table 1 shows an example of the analysis result of the microscopic image of FIG. 23.

TABLE 1

| ID of sample | BioFerm-Yeast-2e7-wu |
|---|---|
| ID of user | 123 |
| Concentration of alive yeast | 1.83E+07 |
| Total concentration of yeast | 1.92E+07 |
| Mortality rate of yeast | 4.3% |
| Concentration of dead yeast | 8.24E+05 |
| Total count of yeast | 3791 |
| Count of alive yeast | 3628 |
| Count of dead yeast | 163 |
| Average diameter (μm) | 7.93 |
| Average circularity | 0.78 |
| Aggregation rate | 58.69% |
| Type of yeast | Beer yeast |

As shown in Table 1, the type of yeast in the microscopic image of FIG. 19 is beer yeast. The image processing device may count the live yeast and dead yeast in the microscopic image, so that the count of alive yeast is 3628 and the count of dead yeast is 163. Thus, the total count of yeast=the count of alive yeast+the count of dead yeast=3791, the mortality rate of yeast=the count of dead yeast/ the total count of yeast=4.3%.

In addition, as described above, the image processing device may further obtain the depth of the sample cell (e. g., based on the type of sample plate). Then, based on the depth of the sample cell and the area of the sample cell in the microscopic image (which may be determined based on the magnification), the concentration of the yeast, such as the concentration of alive yeast, the concentration of dead yeast and/or the total concentration of yeast concentration may be determined. That is, the image processing device may determine the concentration of alive yeast, the concentration of dead yeast and/or the total concentration of yeast concentration based on the depth of the sample cell, the count of alive yeast, the count of dead yeast and the magnification.

Figure 25:
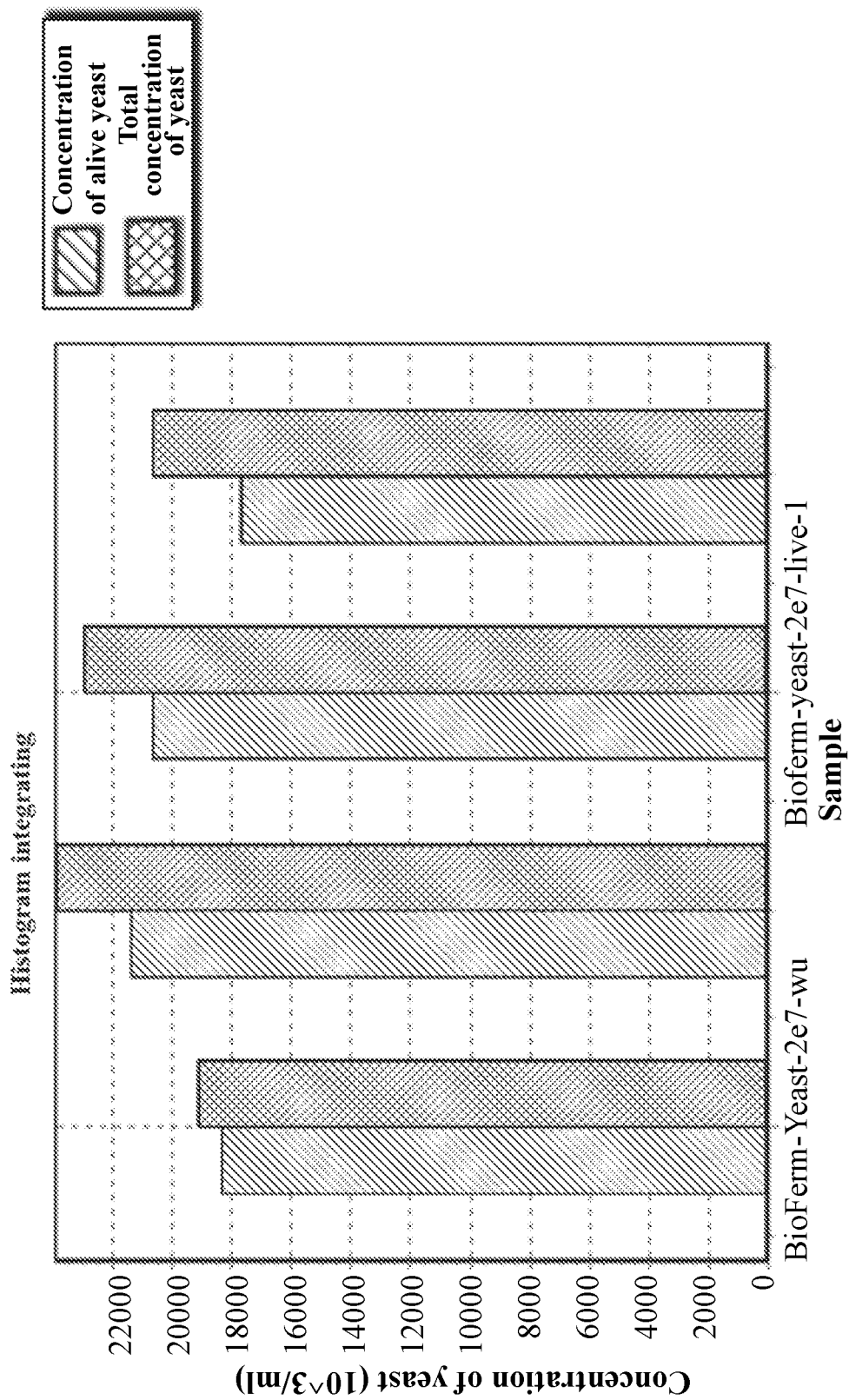
FIG. 25 is a histogram illustrating a concentration of yeast according to some embodiments of the present disclosure.

In addition, the image processing device may generate a histogram based on the microscopic images of a plurality of samples and transmit the histogram to the client. For example, FIG. 25 is a histogram illustrating a concentration of yeast according to some embodiments of the present disclosure. As shown in FIG. 25, the horizontal axis represents different samples and the vertical axis represents concentrations. The concentration of alive yeast and total concentration of yeast of each sample are displayed in FIG. 25, thus the users may intuitively understand and compare the concentration of yeast of each sample.

Figure 24:
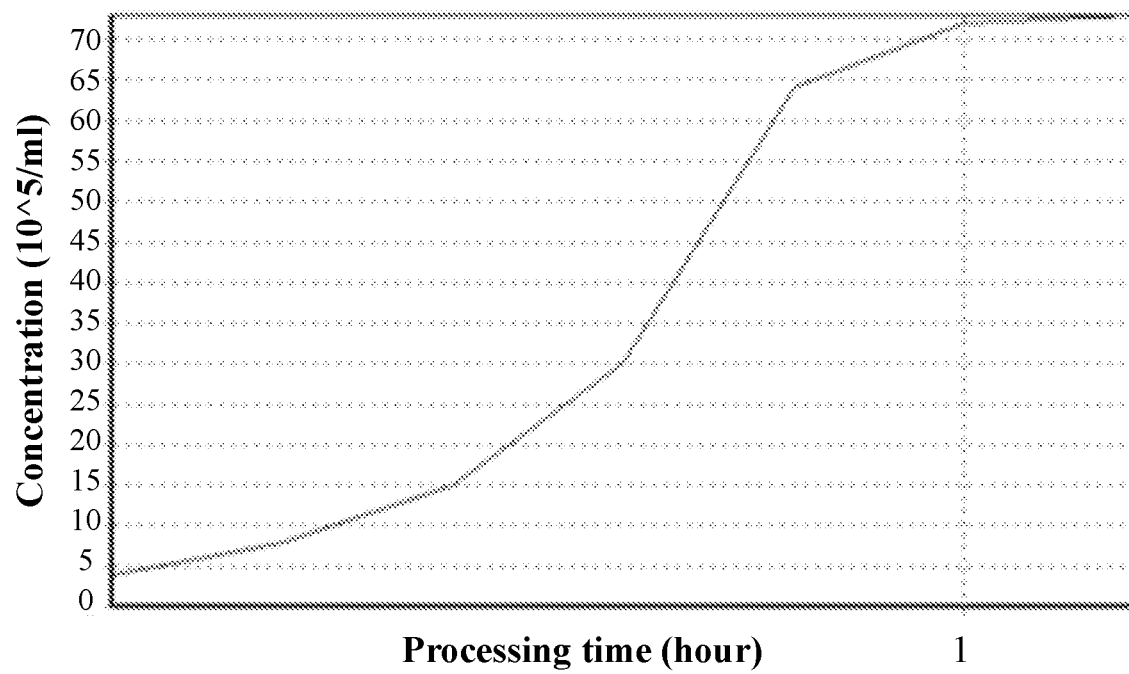
FIG. 24 is a schematic diagram illustrating a CGC curve according to some embodiments of the present disclosure.

In addition, the image processing device may also generate cell growth curve (CGC curve) based on microscopic images of different samples. As shown in FIG. 24, CGC curve is a common way to determine an absolute growth count of cells. The CGC curve may reflect a change of a count of cells with time in the same group of samples.

In addition, the CGC curve may also designate parameters such as a count of yeast (for example, the count of alive yeast, the count of dead yeast, the total count of yeast), the viability rate, the average diameter, the average compactness, the aggregate rate, etc., as the vertical axis, to show a relationship between these parameters and processing time.

In addition, as shown in Table 1, the image processing device may determine diameter of each yeast based on the magnification, and average diameter of yeast may be determined based on the diameter of each yeast and the total count of yeast. In some embodiments, the image processing device may also generate a histogram of the diameter of yeast, so that the user may more clearly and intuitively understand the distribution of the diameter of yeast.

Figure 26:
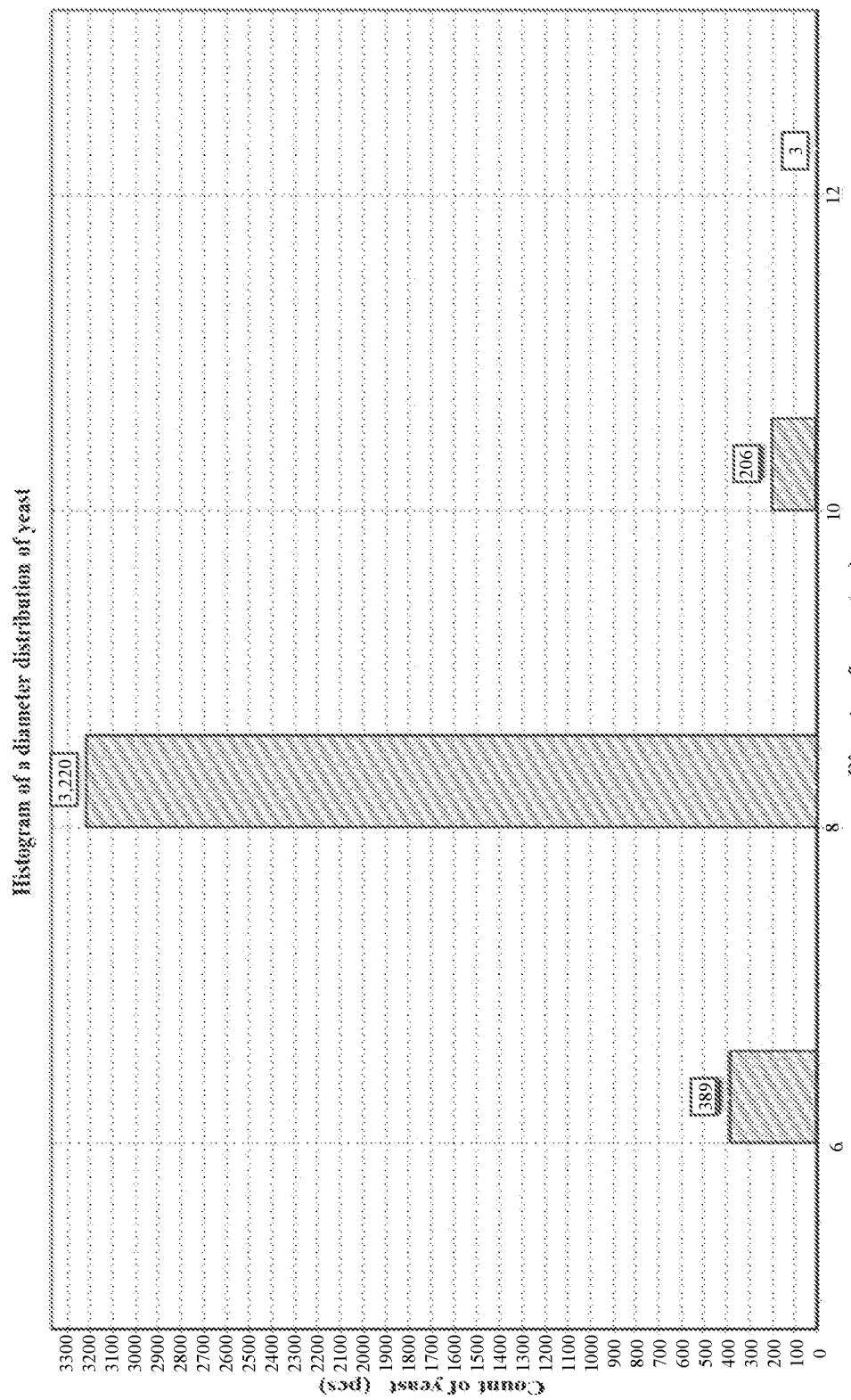
FIG. 26 is a histogram illustrating a diameter distribution of yeast according to some embodiments of the present disclosure.

FIG. 26 is a histogram illustrating the diameter of yeast according to a embodiment of the present disclosure. As shown in FIG. 26, in the histogram of the diameter of yeast, the count of yeast with different diameters is shown, in which a count of yeast with diameter approaching 6 μm is 389, a count of yeast with diameter approaching 8 μm is 3220, a count of yeast with diameter approaching 10 μm is 206, and a count of yeast with diameter approaching 12 μm is 3. According to FIG. 26, it can be seen that the diameter of most yeast is 6-10 μm.

Figure 27:
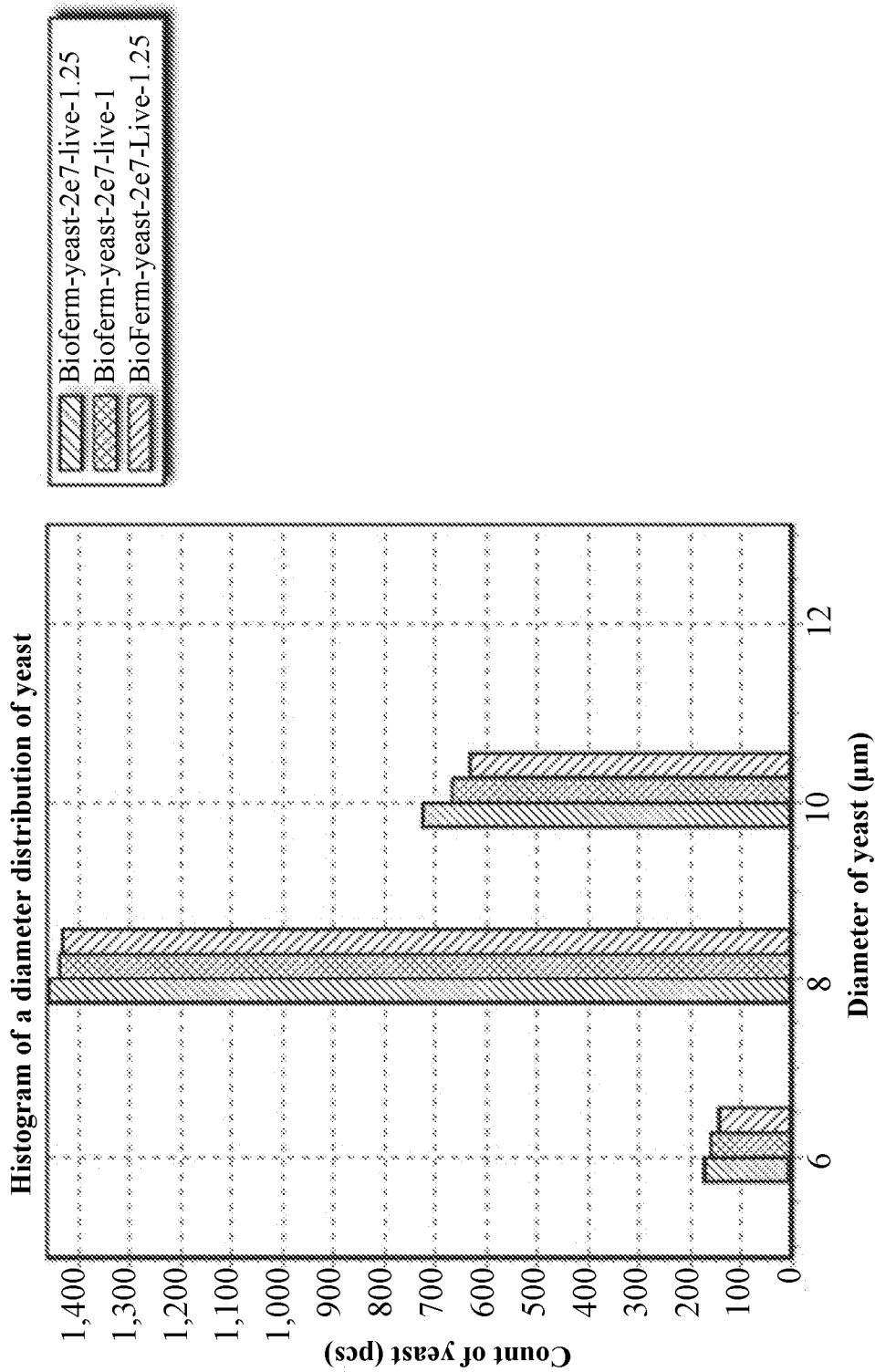
FIG. 27 is another histogram illustrating a diameter distribution of yeast according to some embodiments of the present disclosure.

In addition, since the microscopic images of a plurality of samples are usually stored on the server (such as the cloud server), the histogram of the diameter of yeast of each sample may be integrated to generate an integrated diagram of the diameter of yeast. FIG. 27 is an integrated diagram illustrating the diameter of yeast according to a embodiment of the present disclosure. As shown in FIG. 27, the histogram of the diameter of yeast of three samples is integrated. The diameter of yeast and distribution of different samples may be intuitively compared.

In addition, the image processing device may also determine the count of aggregated yeast by performing an image processing operation on the microscopic image, and the aggregation rate may be determined based on the total count of yeast and the count of the aggregated yeast. For example, the image processing device may identify a count of yeast aggregates, a count of yeast in each yeast aggregate based on the image processing operation, so the aggregation rate may be determined as follows the aggregation rate of yeast=($\Sigma$ the count of yeast in each yeast aggregate)/the total count of yeast.

Figure 28:
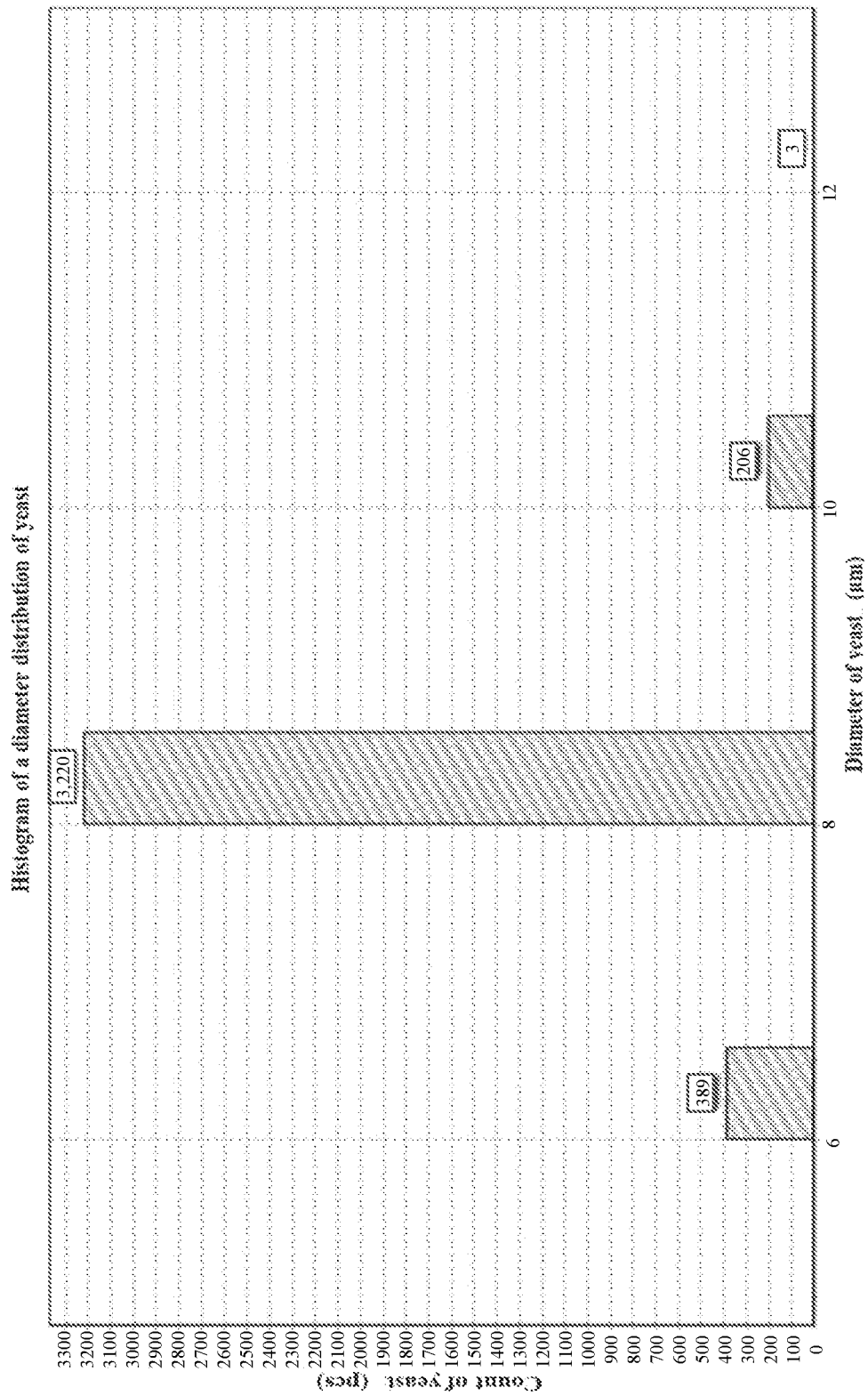
FIG. 28 is a histogram illustrating yeast aggregates according to some embodiments of the present disclosure.

In addition, the image processing device may also generate a histogram of yeast aggregates. FIG. 28 is a histogram illustrating yeast aggregates according to a embodiment of the present disclosure. As shown in FIG. 28, in the histogram of yeast aggregates, the abscissa is the count of yeast in a yeast aggregate, and the ordinate is the count of the yeast aggregates. As shown in FIG. 28, for the microscopic image of the sample of yeast shown in FIG. 23, the count of yeast aggregates including 2 yeast is 423, the count of yeast aggregates including 3 yeast is 146, the count of yeast aggregates including 4 yeast is 85, the count of yeast aggregates including 5 yeast is 43, the count of yeast aggregates including 6 yeast is 19, the count of yeast aggregates including 7 yeast is 14, the count of yeast aggregates including 8 yeast is 8, the count of yeast aggregates including 9 yeast is 6, the count of yeast aggregates including 10 yeast is 2, the count of yeast aggregates including 11 yeast is 2, the count of yeast aggregates including 12 yeast is 2, the count of yeast aggregates including 13 yeast is 1, and the count of yeast aggregates including 14 yeast is 1. As shown in FIG. 28, in the case of yeast agglomeration, most yeast aggregates may include 2-5 yeast.

In addition to the histogram described above, the image processing device may also generate other types of diagrams, such as a pie chart, or the like.

In addition, the image processing device may perform an image processing operation on the microscopic image to determine other parameters. For example, the circularity of each yeast may be determined by the image processing operation, and the average circularity of yeast may be determined based on the circularity of each yeast and the total count of yeast.

In some embodiments according to the present disclosure, the image processing device may also perform an image processing operation on the microscopic image to determine the count of budding yeast, and the bud rate of yeast may be determined based on the total count of yeast and the count of budding yeast. The bud rate is one of the important quality standards reflecting the growth of yeast. For example, in some embodiments, a yeast with a bud volume less than ½ of the mother yeast may be used as a budding yeast, and a yeast with a bud volume greater than ½ of the mother yeast may be used as two yeast, and then the bud rate of yeast may be determined as follows the bud rate of yeast=the budding yeast/the total count of yeast.

In addition, as described above, the server may be, for example, a remote server or a cloud server, and the image processing device may be, for example, an image processing module running on the remote server or the cloud server. In the embodiment of the present disclosure, since the magnification may be accurately determined based on the ruler pattern on the microscopic image, the microscopic images captured by different microscopic devices may be compared, and a integrated diagram of the histogram of the diameter of yeast as described above may be generated.

In addition, in some embodiments according to the present disclosure, the following technical schemes may also be adopted:

1. A method for analysis of yeast, comprising:
receiving a microscopic image of yeast by a cloud server, wherein the microscopic image includes a scaling pattern for determining a magnification;
determining the magnification by the cloud server based on the scaling pattern; and
analyzing, by the cloud server, the microscopic image based on the magnification to obtain an analysis result.

2. The method for analysis of yeast of claim 1, wherein the analysis result includes at least one of a concentration of alive yeast, a concentration of dead yeast, a total concentration of the yeast, a mortality rate of the yeast, a survival rate of the yeast, an average diameter of the yeast, an average circularity of the yeast, a bud rate of the yeast, or an aggregation rate.

3. The method for analysis of yeast of claim 2, wherein the analyzing the microscopic image based on the magnification comprises:
performing, by the cloud server, an image processing operation on the microscopic image to determine a count of the alive yeast and a count of the dead yeast in the microscopic image.

4. The method for analysis of yeast of claim 3, further comprising:
capturing the microscopic image of the yeast in a sample cell on a sample plate by a microscopic device and transmitting the microscopic image to the cloud server;
obtaining a depth of the sample cell by the cloud server; and
determining, by the cloud server, the total concentration of the yeast, the concentration of the alive yeast, the concentration of the dead yeast based on the depth of the sample cell, the count of the alive yeast, the count of the dead yeast and the magnification.

5. The method for analysis of yeast of claim 3, wherein the cloud server determines the concentration of the alive yeast based on the count of the alive yeast and the count of the dead yeast.

6. The method for analysis of yeast of claim 2, wherein the analyzing the microscopic image based on the magnification includes:
determining a diameter of each yeast and a total count of the yeast by the cloud server based on the magnification; and
determining the average diameter of the yeast based on the diameter of each yeast and the total count of the yeast.

7. The method for analysis of yeast of claim 2, wherein the cloud server performs an image processing operation on the microscopic image to determine a circularity of each yeast and the total count of the yeast, and the cloud server determines the average circularity of the yeast based on the circularity of each yeast and the total count of the yeast.

8. The method for analysis of yeast of claim 2, wherein the cloud server performs an image processing operation on the microscopic image to determine the total count of the yeast and a count of budding yeast, and the cloud server determines the bud rate of the yeast based on the total count of the yeast and the count of the budding yeast.

9. The method for analysis of yeast of claim 2, wherein the cloud server performs an image processing operation on the microscopic image to determine the total count of the yeast and a count of aggregated yeast, and the cloud server determines the aggregation rate based on the total count of the yeast and the count of the aggregated yeast.

10. The method for analysis of yeast of claim 1, further comprising:
capturing the microscopic image of the yeast in a sample cell on a sample plate by a microscopic device and transmitting the microscopic image to the cloud server.

11. The method for analysis of yeast of claim 10, wherein the sample plate includes the scaling pattern.

12. The method for analysis of yeast of claim 11, wherein the scaling pattern is located at the bottom of the sample cell.

13. The method for analysis of yeast of claim 12, wherein the sample plate includes a plurality of sample cells, and the scaling pattern is arranged at the bottom of each sample cell.

14. The method for analysis of yeast of claim 11, wherein the scaling pattern is located near the sample cell.

15. The method for analysis of yeast of any one of claims 11-14, wherein the scaling pattern includes a first tick mark extending in a first direction.

16. The method for analysis of yeast of claim 15, wherein the scaling pattern includes a plurality of first tick marks, and the plurality of first tick mark are arranged in a second direction that is different from the first direction.

17. The method for analysis of yeast of claim 16, wherein the first direction is perpendicular to the second direction.

18. The method for analysis of yeast of claim 16 or claim 17, wherein the sample cell extends in the first direction or the second direction.

19. The method for analysis of yeast of any one of claims 16-18, wherein the scaling pattern further includes a second tick mark extending in the second direction.

20. The method for analysis of yeast of any one of claims 11-19, wherein the scaling pattern further includes a first mark for determining an extension direction and an arrangement direction of the sample cell.

21. The method for analysis of yeast of claim 20, wherein the first mark includes a first arrow and a second arrow, which are perpendicular to each other.

22. The method for analysis of yeast of any one of claims 11-21, wherein the scaling pattern further includes a second mark for identifying the sample plate.

23. The method for analysis of yeast of claim 22, wherein the scaling pattern further includes a third mark for identifying the sample cell.

24. The method for analysis of yeast of claim 22, wherein obtaining the depth of the sample cell includes determining the depth of the sample cell on the sample plate based on the second mark.

25. The method for determining a count of the yeast of claim 23, wherein obtaining the depth of the sample cell includes determining the depth of the sample cell on the sample plate based on the third mark.

The terms "front", "back", "top", "bottom", "over", and "under" in the present disclosure and claims, if present, are used for descriptive purposes and are not necessarily used to describe invariant relative positions. It is to be understood that the terms so used are interchangeable under appropriate circumstances, enabling the embodiments of the disclosure described herein. For example, capable of operating in other orientations than those shown or otherwise described herein.

As used herein, the term "exemplary" means "serving as an example, instance, or illustration" rather than as a "model" to be exactly reproduced. Any implementation illustratively described herein is not necessarily to be construed as preferred or advantageous over other implementations. Furthermore, the present disclosure is not to be bound by any expressed or implied theory presented in the preceding technical field, background, summary, or detailed description.

As used herein, the term "substantially" is meant to encompass any minor variation due to design or manufacturing imperfections, tolerances of devices or elements, environmental influences, and/or other factors. The term "substantially" also allows for differences from a perfect or ideal situation due to parasitic effects, noise, and other practical considerations that may exist in an actual implementation.

The above description may indicate elements or nodes or features that are "connected" or "coupled" together. As used herein, unless expressly stated otherwise, "connected" means that one element/node/feature is electrically, mechanically, logically, or otherwise directly connected to another element/node/feature (or direct communication). Similarly, unless expressly stated otherwise, "coupled" means that one element/node/feature can be mechanically, electrically, logically, or otherwise linked, directly or indirectly, with another element/node/feature to Interactions are allowed, even though the two features may not be directly connected. That is, "coupled" is intended to encompass both direct and indirect coupling of elements or other features, including connections that utilize one or more intervening elements.

In addition, certain terms may also be used in the following description for reference purposes only, and are thus not intended to be limiting. For example, the terms "first," "second," and other such numerical terms referring to structures or elements do not imply a sequence or order unless the context clearly dictates otherwise.

It should also be understood that the word "including/comprising" is used herein to indicate the presence of the indicated features, integers, steps, operations, units, and/or components, but does not preclude the presence or addition of one or more other features, integers, steps, operations, units and/or components and/or combinations thereof.

In the present disclosure, the term "providing" is used in a broad sense to encompass all manners of obtaining an object, thus "providing something" includes, but is not limited to, "purchasing," "preparing/manufacturing," "arranging/setting," "installing/assembling," and/or "ordering" the objects, etc.

Those skilled in the art should appreciate that the boundaries between the operations described above are merely illustrative. Multiple operations may be combined into a single operation, a single operation may be distributed among additional operations, and operations may be performed at least partially overlapping in time. Furthermore, alternative embodiments may include multiple instances of a particular operation, and the order of operations may be changed in other various embodiments. However, other modifications, changes, and substitutions are equally possible. Accordingly, the present disclosure and drawings are to be regarded in an illustrative rather than a restrictive sense.

Although some specific embodiments of the present disclosure have been described in detail by way of examples, those skilled in the art should understand that the above examples are for illustration only, and not for the purpose of limiting the scope of the present disclosure. The various embodiments disclosed herein may be combined in any combination without departing from the spirit and scope of the present disclosure. It will also be understood by those skilled in the art that various modifications may be made to the embodiments without departing from the scope and spirit of the present disclosure. The scope of the present disclosure is defined by the claims.

What is claimed is:

1. A method for analysis of yeast, comprising:
capturing a microscopic image of yeast in a sample cell on a sample plate by a microscopic device;
transmitting the microscopic image to a cloud server;
receiving the microscopic image including the yeast and pattern information related to the microscopic image by the cloud server, wherein the microscopic image includes a scaling pattern for determining a magnification, and the pattern information is associated with the scaling pattern;
determining the magnification by the cloud server based on the scaling pattern and the pattern information; and analyzing, by the cloud server, the microscopic image based on the magnification to obtain an analysis result, wherein the sample plate includes the scaling pattern, the scaling pattern including a first mark for determining an extension direction and an arrangement direction of the sample cell. a second mark for identifying the sample plate, a third mark for identifying the sample cell, and two line segments that are perpendicular to each other, and the method for analysis of yeast further comprises correcting the microscopic image based on the scaling pattern in the microscopic image and the scaling pattern on the sample plate.

2. The method for analysis of yeast of claim 1, wherein the analysis result includes at least one of a concentration of alive yeast, a concentration of dead yeast, a total concentration of the yeast, a mortality rate of the yeast, a survival rate of the yeast, an average diameter of the yeast, an average circularity of the yeast, a bud rate of the yeast, and an aggregation rate.

3. The method for analysis of yeast of claim 2, wherein the analyzing the microscopic image based on the magnification comprises:

performing, by the cloud server, an image processing operation on the microscopic image to determine a count of the alive yeast and a count of the dead yeast in the microscopic image.

4. The method for analysis of yeast of claim 3, further comprising:

obtaining a depth of the sample cell by the cloud server; and determining, by the cloud server, the total concentration of the yeast, the concentration of the alive yeast, and the concentration of the dead yeast based on the depth of the sample cell, the count of the alive yeast, the count of the dead yeast and the magnification.

5. The method for analysis of yeast of claim 4, wherein obtaining the depth of the sample cell includes determining the depth of the sample cell on the sample plate based on the second mark.

6. The method for analysis of yeast of claim 4, wherein obtaining the depth of the sample cell includes determining the depth of the sample cell on the sample plate based on the third mark.

7. The method for analysis of yeast of claim 3, wherein the cloud server determines the concentration of the alive yeast based on the count of the alive yeast and the count of the dead yeast.

8. The method for analysis of yeast of claim 2, wherein the analyzing the microscopic image based on the magnification includes:

determining a diameter of each yeast and a total count of the yeast by the cloud server based on the magnification; and determining the average diameter of the yeast based on the diameter of each yeast and the total count of the yeast.

9. The method for analysis of yeast of claim 2, wherein the cloud server performs an image processing operation on the microscopic image to determine a circularity of each yeast and the total count of the yeast, and the cloud server determines the average circularity of the yeast based on the circularity of each yeast and the total count of the yeast.

10. The method for analysis of yeast of claim 2, wherein the cloud server performs an image processing operation on the microscopic image to determine the total count of the yeast and a count of budding yeast, and the cloud server determines the bud rate of the yeast based on the total count of the yeast and the count of the budding yeast.

11. The method for analysis of yeast of claim 2, wherein the cloud server performs an image processing operation on the microscopic image to determine the total count of the yeast and a count of aggregated yeast, and the cloud server determines the aggregation rate based on the total count of the yeast and the count of the aggregated yeast.

12. The method for analysis of yeast of claim 1, wherein the scaling pattern is located at the bottom of the sample cell.

13. The method for analysis of yeast of claim 12, wherein the sample plate includes a plurality of sample cells, and the scaling pattern is arranged at the bottom of each sample cell.

14. The method for analysis of yeast of claim 1, wherein the scaling pattern is located near the sample cell.

15. The method for analysis of yeast of claim 1, wherein the scaling pattern includes a first tick mark extending in a first direction.

16. The method for analysis of yeast of claim 15, wherein the scaling pattern includes a plurality of first tick marks, and the plurality of first tick mark are arranged in a second direction that is different from the first direction.

17. The method for analysis of yeast of claim herein the first direction is perpendicular to the second direction.

18. The method for analysis of yeast of claim 16, wherein the sample cell extends in the first direction or the second direction.

19. The method for analysis of yeast of claim 16, wherein the scaling pattern further includes a second tick mark extending in the second direction.

20. The method for analysis of yeast of claim 1, wherein the first mark includes a first arrow and a second arrow, which are perpendicular to each other.

* * * * *